(12) United States Patent
Yao et al.

(10) Patent No.: US 11,066,457 B2
(45) Date of Patent: Jul. 20, 2021

(54) CONSTRUCTION OF CHIMERIC ANTIGEN RECEPTOR TARGETING CD20 ANTIGEN AND ACTIVITY IDENTIFICATION OF ENGINEERED T CELLS THEREOF

(71) Applicant: Cellular Biomedicine Group HK Limited, Hong Kong (CN)

(72) Inventors: Yihong Yao, Shanghai (CN); Jiaqi Huang, Shanghai (CN); Shigui Zhu, Shanghai (CN); Wei Zhu, Shanghai (CN); Xin Yao, Shanghai (CN); Zhiyuan Li, Shanghai (CN); Li Zhang, Shanghai (CN); Lin Zhu, Shanghai (CN); Anyun Ma, Shanghai (CN); Yutian Wei, Shanghai (CN); Yanfeng Li, Shanghai (CN); Qingxia Wang, Shanghai (CN); Jiaping He, Shanghai (CN)

(73) Assignee: CELLULAR BIOMEDICINE GROUP HK LIMITED, Hong Kong (CN)

( * ) Notice: Subject to any disclaimer, the term of this patent is extended or adjusted under 35 U.S.C. 154(b) by 0 days.

(21) Appl. No.: 16/484,482

(22) PCT Filed: Feb. 8, 2018

(86) PCT No.: PCT/CN2018/075867
§ 371 (c)(1),
(2) Date: Aug. 8, 2019

(87) PCT Pub. No.: WO2018/145649
PCT Pub. Date: Aug. 16, 2018

(65) Prior Publication Data
US 2020/0002400 A1    Jan. 2, 2020

(30) Foreign Application Priority Data
Feb. 8, 2017 (CN) .......................... 201710069569.7

(51) Int. Cl.
| | |
|---|---|
| *A61K 35/17* | (2015.01) |
| *A61P 35/02* | (2006.01) |
| *C12N 5/10* | (2006.01) |
| *C07K 16/28* | (2006.01) |
| *C12N 15/62* | (2006.01) |
| *C07K 14/705* | (2006.01) |
| *C07K 14/725* | (2006.01) |
| *A61P 35/00* | (2006.01) |
| *C12N 7/00* | (2006.01) |
| *C12N 15/86* | (2006.01) |
| *C07K 19/00* | (2006.01) |
| *A61K 38/00* | (2006.01) |
| *A61K 39/00* | (2006.01) |

(52) U.S. Cl.
CPC .......... *C07K 14/7051* (2013.01); *A61K 35/17* (2013.01); *A61P 35/00* (2018.01); *A61P 35/02* (2018.01); *C07K 14/70517* (2013.01); *C07K 14/70521* (2013.01); *C07K 14/70578* (2013.01); *C07K 16/2887* (2013.01); *C07K 19/00* (2013.01); *C12N 5/10* (2013.01); *C12N 7/00* (2013.01); *C12N 15/62* (2013.01); *C12N 15/86* (2013.01); *A61K 38/00* (2013.01); *A61K 2039/505* (2013.01); *C07K 2317/524* (2013.01); *C07K 2317/526* (2013.01); *C07K 2317/53* (2013.01); *C07K 2317/622* (2013.01); *C07K 2317/732* (2013.01); *C07K 2317/76* (2013.01); *C07K 2319/02* (2013.01); *C07K 2319/03* (2013.01); *C07K 2319/30* (2013.01); *C07K 2319/33* (2013.01); *C12N 2740/15043* (2013.01)

(58) Field of Classification Search
None
See application file for complete search history.

(56) References Cited

U.S. PATENT DOCUMENTS

| | | | |
|---|---|---|---|
| 6,410,319 | B1 | 6/2002 | Raubitschek et al. |
| 8,287,864 | B2 | 10/2012 | Goldenberg et al. |
| 8,329,181 | B2 | 12/2012 | Martin et al. |
| 8,529,902 | B2 | 9/2013 | Teeling et al. |
| 9,834,590 | B2 | 12/2017 | Campana et al. |
| 10,525,083 | B2 | 1/2020 | Brannetti et al. |
| 10,603,380 | B2 | 3/2020 | Wilzius |

(Continued)

FOREIGN PATENT DOCUMENTS

| | | |
|---|---|---|
| CN | 101544694 A | 9/2009 |
| WO | 00/23573 A2 | 4/2000 |

(Continued)

OTHER PUBLICATIONS

Jonnalagadda et al. Chimeric Antigen Receptors With Mutated IgG4 Fc Spacer Avoid Fc Receptor Binding and Improve T Cell Persistence and Antitumor Efficacy. Molecular Therapy 2015; vol. 23 No. 4, 757-768.*

(Continued)

*Primary Examiner* — Ilia I Ouspenski

(74) *Attorney, Agent, or Firm* — Leason Ellis LLP

(57) ABSTRACT

Provided are a chimeric antigen receptor targeting CD20 antigen and a preparation method thereof. The extracellular antigen binding domain of the chimeric antigen receptor includes an antibody heavy chain variable region shown in SEQ ID NO: 7 or 9 or 33 and an antibody light chain variable region shown in SEQ ID NO: 11 or 13 or 35, and is capable of killing tumor cells.

8 Claims, 4 Drawing Sheets
Specification includes a Sequence Listing.

(56) References Cited

U.S. PATENT DOCUMENTS

| | | | |
|---|---|---|---|
| 2004/0167319 A1* | 8/2004 | Teeling | A61P 37/06 530/388.22 |
| 2009/0148447 A1* | 6/2009 | Ledbetter | C07K 16/2833 424/134.1 |
| 2011/0091473 A1* | 4/2011 | Golab | A61K 45/06 424/152.1 |
| 2013/0004480 A1* | 1/2013 | Parren | C07K 16/2887 424/132.1 |
| 2013/0224205 A1* | 8/2013 | Hofmeister | A61P 37/06 424/136.1 |
| 2014/0093454 A1 | 4/2014 | Teeling et al. | |
| 2014/0154253 A1* | 6/2014 | Ng | A61P 29/00 424/136.1 |
| 2015/0038684 A1* | 2/2015 | Jensen | C07K 16/2896 530/391.9 |
| 2016/0158359 A1 | 6/2016 | Gilbert | |
| 2016/0333108 A1* | 11/2016 | Forman | C07K 16/30 |
| 2016/0362472 A1* | 12/2016 | Bitter | C07K 16/2803 |
| 2017/0275382 A1* | 9/2017 | Poma | C07K 16/28 |
| 2017/0368098 A1* | 12/2017 | Chen | C07K 14/70521 |
| 2018/0044415 A1* | 2/2018 | Escarpe | A61K 35/17 |
| 2018/0118823 A1* | 5/2018 | Thompson | C07K 16/468 |
| 2018/0125892 A1* | 5/2018 | Brannetti | A61K 35/17 |
| 2018/0142035 A1* | 5/2018 | Lobb | C07K 16/2803 |
| 2018/0230225 A1* | 8/2018 | Fan | A61P 35/02 |
| 2019/0106501 A1* | 4/2019 | Press | A61P 35/00 |
| 2019/0144515 A1 | 5/2019 | Sievers et al. | |
| 2020/0040096 A1 | 2/2020 | Forman et al. | |
| 2020/0093861 A1 | 3/2020 | Klein et al. | |
| 2020/0308223 A1* | 10/2020 | Chang | A61K 47/547 |

FOREIGN PATENT DOCUMENTS

| | | |
|---|---|---|
| WO | 2016/097231 A2 | 6/2016 |
| WO | 2016/166521 A1 | 10/2016 |
| WO | 2019/129177 A1 | 7/2019 |
| WO | 2020/010235 A1 | 1/2020 |

OTHER PUBLICATIONS

Belovezhec T.N. Design and Comparative Analysis of CD20-Specific Chimeric Antigen Receptors. Proceedings of XIV International Conference of Students, Graduate Students and Young Scientists "Perspectives in Fundamental Sciences" Apr. 25-28, 2017. vol. 4: Biology and Basic Medical Sciences p. 22-24 (in Russian.*

Belovezhec T.N. Design and Comparative Analysis of CD20-Specific Chimeric Antigen Receptors. Proceedings of XIV International Conference of Students, Graduate Students and Young Scientists "Perspectives in Fundamental Sciences" Apr. 25-28, 2017. English translation, 3 pages.*

Lopez-Atalaya et al. Development and Maintenance of the Brain's Immune Toolkit: Microglia and Non-Parenchymal Brain Macrophages. Dev Neurobiol. 2018; 78(6): 561-579.*

Riaz et al. Anti-CD 19 and anti-CD 20 CAR-modified T cells for B-cell malignancies: a systematic review and meta-analysis. Immunotherapy (2017) 9(12), 979-993.*

Nakagawa et al. *Staphylococcus aureus* Virulent PSMa Peptides Induce Keratinocyte Alarmin Release to Orchestrate IL-17-Dependent Skin Inflammation. Cell Host & Microbe 2017; 22, 667-677.*

Ramos et al. CAR-T Cell Therapy for Lymphoma. Annu. Rev. Med. 2016; 67: 165-183.*

Shetty et al. Liver sinusoidal endothelial cells—gatekeepers of hepatic immunity. Nat Rev Gastroenterol Hepatol. 2018; 15(9): 555-567.*

NCBI Accession AMZ04820, 2016, 1 page.*

NCBI Accession ANS59202, 2016, 1 page.*

Teeling et al. The Biological Activity of Human CD20 Monoclonal Antibodies Is Linked to Unique Epitopes on CD20. J Immunol 2006; 177: 362-371.*

Korycka-Wolowiec et al. Ofatumumab for treating chronic lymphocytic leukemia: a safety profile. Expert Opinion on Drug Safety 2015; 14(12): 1945-1959.*

Jabbour et al. Monoclonal antibodies in acute lymphoblastic leukemia. Blood 2015; 125(26): 4010-4016.*

Chuda et al. Ofatumumab: A Novel Anti-CD20 Monoclonal Antibody for the Treatment of Chronic Lymphocytic Leukemia. Current Drug Therapy, 2012, 7, 281-289.*

Till et al. (2012). CD20-specific adoptive immunotherapy for lymphoma using a chimeric antigen receptor with both CD28 and 4-1BB domains: pilot clinical trial results. Blood 119: 3940-3950.*

U.S. Appl. No. 16/877,069, filed Mar. 2020, Yao, Yihong.*

Teeling et al. (2004) Characterization of new human CD20 monoclonal antibodies with potent cytolytic activity against non-Hodgkin lymphomas. Blood 104: 1793-1800.*

Lin TS (2010) Ofatumumab: a novel monoclonal anti-CD20 antibody. Pharmacogenomics and Personalized Medicine 3: 51-59.*

Casan et al. (2018) Anti-CD20 monoclonal antibodies: reviewing a revolution. Human Vaccines & Immunotherapeutics 14(12): 2820-2841.*

Till et al. (2012) CD20-specific adoptive immunotherapy for lymphoma using a chimeric antigen receptor with both CD28 and 4-1BB domains: pilot clinical trial results. Blood 119(17): 3940-3950.*

Hamdy et al. (2005) Sheep red blood cells armed with anti-CD20 single-chain variable fragments (scFvs) fused to a glycosylphosphatidylinositol (GPI) anchor: a strategy to target CD20-positive tumor cells. J. Immunol. Methods 297(1-2): 109-124.*

GenBank Accession AAO22134.1 (2005), 2 pages.*

Wu et al. (2001) Multimerization of a chimeric anti-CD20 single-chain Fv—Fc fusion protein is mediated through variable domain exchange. Protein Eng. 14: 1025-1033.*

Lulla et al. (2018) The Use of Chimeric Antigen Receptor T Cells in Patients with Non-Hodgkin Lymphoma, Clinical Advances in Hematology & Oncology, 16(5): 375-386.*

Hallek M. (2017) Chronic lymphocytic leukemia: 2017 update on diagnosis, risk stratification, and treatment. Am J Hematol. 92: 946-965.*

Cao et al. (2019) Efficiency and safety of autologous chimeric antigen receptor T-cells therapy used for patients with lymphoma. Medicine 98: 42(e17506), 8 pages (provided by applicant).*

Till et al. (2008) Adoptive immunotherapy for indolent non-Hodgkin lymphoma and mantle cell lymphoma using genetically modified autologous CD20-spetific T cells. Blood 112(6): 2261-2271 (provided by applicant).*

Wang et al. (2014) Effective response and delayed toxicities of refractory advanced diffuse large B-cell lymphoma treated by CD20-directed chimeric antigen receptor-modified T cells. Clinical Immunology 155: 160-175 (provided by applicant).*

Zhang et al. (2016) Treatment of CD20-directed Chimeric Antigen Receptor-modified T cells in patients with relapsed or refractory B-cell non-Hodgkin lymphoma: an early phase IIa trial report. Signal Transduction and Targeted Therapy 1: 16002; p. 1-10 (provided by applicant).*

Jensen et al. (1998) CD20 is a molecular target for scFvFc:zeta receptor redirected T-cells: implications for cellular immunotherapy of CD20 malignancy. Biology of Blood and Marrow Transplant 4: 75-83 (provided by applicant).*

Chow et al. (2019) Outcomes of patients with large B-cell lymphomas and progressive disease following CD19-specific CAR T-cell therapy. Am. J. Hematol. 94(8): E209-E213 (provided by applicant).*

Rufener, Gregory A. et al., "Preserved Activity of CD20-Specific Chimeric Antigen Receptor-Expressing T Cells in the Presence of Rituximab," Cancer Immunology Research, 4(6), Jun. 2016, pp. 509-519.

Wang, D. et al., "GenBank Accession No. AKH40187, Version AKH40187.1," GenBank, Jul. 28, 2015, 2 pages.

International Search Report dated May 9, 2018 for PCT/CN2018/075867.

International Search Report/Written Opinion dated May 9, 2018 for PCT/CN2018/075867.

(56) References Cited

OTHER PUBLICATIONS

Lihua E. Budde et al., Combining a CD20 Chimeric Antigen Receptor and an Inducible Caspase 9 Suicide Switch to Improve the Efficacy and Safety of T Cell Adoptive Immunotherapy for Lymphoma, PLOS ONE, vol. 8, No. 12, 2013, pp. 1-10.

Ku Matthew et al., Tumour cell surface antigen targeted therapies in B-cell lymphomas: Beyond rituximab, Blood Reviews, vol. 31, No. 1, 2016, pp. 23-35.

Andrew D. Fesnak et al., Engineered T Cells: The Promise and Challenges of Cancer Immunotherapy, Nature Reviews Cancer, vol. 16, No. 9, 2016, pp. 566-581.

Extended European Search Report in EP18751050.8, dated Oct. 15, 2020.

\* cited by examiner

CONSTRUCTION OF CHIMERIC ANTIGEN RECEPTOR TARGETING CD20 ANTIGEN AND ACTIVITY IDENTIFICATION OF ENGINEERED T CELLS THEREOF

CROSS REFERENCE TO RELATED APPLICATIONS

This application is the National Stage of International Application No. PCT/CN2018/075867, filed Feb. 8, 2018, and claims benefit of Chinese Application No. 201710069569.7 filed on Feb. 8, 2017, both of which are herein incorporated by reference in their entirety.

REFERENCE TO A SEQUENCE LISTING

The instant application contains a sequence listing which has been submitted in ASCII format via EFS-Web and is hereby incorporated by reference in its entirety. Said ASCII copy, created on Aug. 23, 2019, is named 221281_0001_592230_SubSL_ST25.txt and is 66,002 bytes in size.

TECHNICAL FIELD

The present invention provides a sequence component of chimeric antigen receptor targeting CD20 antigen, and a preparation method for its modified T cells (CART20) and activity identification thereof. The present invention identifies a chimeric antigen receptor structure for treating CD20 positive B cell lymphoma.

BACKGROUND TECHNIQUE

Malignant tumors of the blood system account for about 10% of human malignant tumors, and 95% of malignant tumors of the blood system are derived from B lymphocytes. Traditional chemotherapy and radiotherapy play an important role in the treatment of malignant tumors of the blood system. Some patients also have significant effects, but most of them are difficult to cure. New and effective treatments have been a hot topic in this field.

Adoptive T cell therapy has shown its powerful efficacy and bright prospect in the clinical treatment of malignant tumors. Among them, multiple centers independently using Chimeric Antigen Receptor (CAR)-modified T cells to target recurrent, refractory malignant tumors of CD19-expressed B cell have achieved unprecedented success. In particular, in a clinical trial carried out at the School of Medicine, University of Pennsylvania using CART19 in the treatment of recurrent, refractory acute B-cell lymphoma (R/R B-ALL), up to 94% of patients achieved complete remission. Although the initial response rate of this clinical trial was high, nearly 40% of patients who achieved complete response after 1 month of treatment, had a relapse, and more than 60% of patients with relapse had CD19-negative tumor cells escape. Therefore, there is an urgent need to screen out CART structure that target B cell lymphoma-associated antigens other than CD19 to treat patients with malignant lymphoma.

CD20 is a glycosylated protein and is the first identified B cell membrane marker. CD20 is also known as B1, and encoded by the MS4A gene. CD20 molecule has four transmembrane hydrophobic regions, and its N-terminal and C-terminal are located on the cytoplasmic side, thereby forming two closed loops outside the cell, which are respectively called big loop and small loop. CD20 is specifically expressed in more than 95% of normal and cancerous B cells. These cells are in the pre-B cell stage and subsequent developmental stages, and CD20 stops expression until the cells differentiated into plasma cells. Therefore, CD20 is an ideal target for immunotherapy of B cell malignancies.

Rituximab (MabThera®, Rituxan®) is the first generation of chimeric monoclonal antibody targeting CD20 which is firstly approved by the US FDA and the European EMA for treating indolent lymphoma. Rituximab recognizes and binds to the big loop structure of the extracellular domain of CD20, and it kills tumor cells by ADCC-mediated killing effect. However, Rituximab alone shows limited activity and short duration of response, but its combination with chemotherapy can significantly enhance the efficacy of chemotherapy. Rituximab is used for the treatment of lymphoma, and half of the patients have a complete response (CR) or a partial response (PR).

Ofatumumab (Arzerra®) is the first completely humanized CD20 therapeutic antibody. Unlike Rituximab, the epitope recognized by Ofatumumab contains parts of the big loop and the small loop of CD20. At the same time, the tumor killing method of Ofatumumab is mainly through the complement-dependent pathway, followed by ADCC-dependent tumor killing effect.

Obinutuzumab (Gazyvaro®, Gazyva®) is a humanized type II CD20 antibody that reduces fucosylation levels and optimizes FcγRIIIa affinity. Obinutuzumab recognizes and binds to the big loop of the extracellular molecule of CD20, and mediates the killing effect on tumor mainly through the ADCC effect. At the same time, the binding of Obinutuzumab to CD20 molecule also has the effect of inducing apoptosis of tumor cells. As for the NHL that does not respond to Rituximab treatment, Obinutuzumab is combined with bendamustine, a nitrogen mustard drug. The phase III clinical trial found that the duration with no deterioration of combination therapy of Obinutuzumab and bendamustine was twice as long as that of bendamustine therapy alone (the former is 29 months and the latter is 14 months). Obinutuzumab has an overall response rate (ORR, including CR and PR) of 77.3%, and Rituximab is 65.7%.

Compared with therapeutic antibodies, cellular immunotherapy is an emerging and highly effective tumor treatment model, and is a new type of autoimmunolgy treatment for cancer. It is a method for in vitro culture and amplification of immune cells collected from a patient using biotechnology and biological agents, and then the cells are transfused back to the patient to stimulate and enhance the body's autoimmune function, thereby achieving the purpose of treating tumors. The skilled in the art have been working to develop new cellular immunotherapy to increase its efficiency and reduce its side effect. Although many therapeutic antibodies as described above have been developed in these years, their clinical therapeutic effects have not reached the same level of therapeutic effects as CART19. Therefore, the development of CART therapy targeting CD20 has great market value and social significance.

SUMMARY OF THE INVENTION

In view of the differences in affinity and killing mechanisms of the therapeutic antibodies targeting CD20, we constructed a series of chimeric antigen receptors targeting CD20 using the DNA sequences of the antigen-binding regions of different antibodies, and completed the identification of anti-tumor activity and differential comparison of these chimeric antigen receptor engineering T cells in vitro. The invention provides new and effective methods and preparations for clinical application of CAR-T in the treatment of CD20-positive leukemia and lymphoma.

It is an object of the present invention to provide a chimeric antigen receptor targeting CD20, a preparation method and application thereof.

The present invention relates to the construction of a chimeric antigen receptor structure targeting CD20, a preparation method of a chimeric antigen receptor engineered T cell targeting CD20, and activity identification thereof.

In a first aspect of the invention, it provides a chimeric antigen receptor (CAR) (sequence), whose antigen binding domain (i.e., scFv) comprises an antibody heavy chain variable region as shown in SEQ ID NOs: 7 or 9 or 33 and an antibody light chain variable region as shown in SEQ ID NOs: 11 or 13 or 35.

In another preferred embodiment, the antigen binding domain of the chimeric antigen receptor is as follows:

$V_H$-$V_L$ wherein $V_H$ is an antibody heavy chain variable region; $V_L$ is an antibody light chain variable region; and "-" is a linker peptide or a peptide bond.

In another preferred embodiment, the amino acid sequence of the linker peptide is as shown in SEQ ID NO: 15.

In another preferred embodiment, the amino acid sequence of $V_H$ is as shown in SEQ ID NO: 7, and the amino acid sequence of $V_L$ is as shown in SEQ ID NO: 11.

In another preferred embodiment, the amino acid sequence of $V_H$ is as shown in SEQ ID NO: 9, and the amino acid sequence of $V_L$ is as shown in SEQ ID NO: 13.

In another preferred embodiment, the amino acid sequence of $V_H$ is as shown in SEQ ID NO: 33, and the amino acid sequence of $V_L$ is shown in SEQ ID NO: 35.

In another preferred embodiment, the structure of the chimeric antigen receptor is as follows:

L-$V_H$-$V_L$-H-TM-CS-CD3ζ wherein,

L is an optional leader sequence (i.e., signal peptide sequence);

H is a hinge region;

TM is a transmembrane domain;

CS is a co-stimulatory molecule derived from 4-1BB and/or CD28;

CD3ζ is a cytoplasmic signaling sequence derived from CD3ζ;

$V_H$, $V_L$, and "-" are as described above, respectively.

In another preferred embodiment, the sequence of L is as shown in SEQ ID NO: 27.

In another preferred embodiment, the sequence of H is as shown in SEQ ID NO: 17 or 19.

In another preferred embodiment, the sequence of TM comprises a transmembrane region derived from CD8a or CD28, preferably the sequence of TM is as shown in SEQ ID NO: 21 or 37.

In another preferred embodiment, the CS structure is: CD28-4-1BB, wherein CD28 is a co-stimulatory molecule derived from CD28; and 4-1BB is a co-stimulatory molecule derived from 4-1BB.

In another preferred embodiment, the sequence of the co-stimulatory molecule derived from 4-1BB is as shown in SEQ ID NO: 23.

In another preferred embodiment, the sequence of the co-stimulatory molecule derived from CD28 is as shown in SEQ ID NO: 39.

In another preferred embodiment, the sequence of CD3ζ is as shown in SEQ ID NO: 25.

In another preferred embodiment, the sequence of the chimeric antigen receptor is as shown in SEQ ID NOs: 1, 3, 5, 29, or 31.

In a second aspect of the invention, a nucleic acid molecule is provided, encoding the chimeric antigen receptor (CAR) of the first aspect of the invention.

In another preferred embodiment, the nucleic acid molecule comprises a nucleic acid sequence encoding the hinge region selected from the group consisting of:

(a) a polynucleotide encoding a polypeptide as shown in SEQ ID NO: 17 or 19;

(b) a polynucleotide having a sequence as shown in SEQ ID NO: 18 or 20;

(c) a polynucleotide having a nucleotide sequence with ≥90% (preferably ≥95%) homologous to the sequence of SEQ ID NO: 18 or 20, and encoding the amino acid sequence of SEQ ID NO: 17 or 19;

(d) a polynucleotide complementary to the polynucleotide of any of (a) to (c).

In another preferred embodiment, the nucleic acid molecule comprises a nucleic acid sequence encoding the CD8a transmembrane region selected from the group consisting of:

(a) a polynucleotide encoding a polypeptide as shown in SEQ ID NO: 21;

(b) a polynucleotide having a sequence as shown in SEQ ID NO: 22;

(c) a polynucleotide having a nucleotide sequence with ≥90% (preferably ≥95%) homologous to the sequence of SEQ ID NO: 22 and encoding the amino acid sequence of SEQ ID NO: 21;

(d) a polynucleotide complementary to the polynucleotide of any of (a) to (c).

In another preferred embodiment, the nucleic acid molecule comprises a nucleic acid sequence encoding the 4-1BB (CD137) intracellular signal domain selected from the group consisting of:

(a) a polynucleotide encoding a polypeptide as shown in SEQ ID NO: 23;

(b) a polynucleotide having a sequence as shown in SEQ ID NO: 24;

(c) a polynucleotide having a nucleotide sequence with ≥90% (preferably ≥95%) homologous to the sequence of SEQ ID NO: 24 and encoding the amino acid sequence of SEQ ID NO: 23;

(d) a polynucleotide complementary to the polynucleotide of any of (a) to (c).

In another preferred embodiment, the nucleic acid molecule comprises a nucleic acid sequence encoding the CD28 intracellular signal domain selected from the group consisting of:

(a) a polynucleotide encoding a polypeptide as shown in SEQ ID NO: 39;

(b) a polynucleotide having a sequence as shown in SEQ ID NO: 40;

(c) a polynucleotide having a nucleotide sequence with ≥90% (preferably ≥95%) homologous to the sequence of SEQ ID NO: 40 and encoding the amino acid sequence of SEQ ID NO: 39;

(d) a polynucleotide complementary to the polynucleotide of any of (a) to (c).

In another preferred embodiment, the nucleic acid molecule comprises a nucleic acid sequence encoding the CD3ζ intracellular signal domain selected from the group consisting of:

(a) a polynucleotide encoding a polypeptide as shown in SEQ ID NO: 25;

(b) a polynucleotide having a sequence as shown in SEQ ID NO: 26;

(c) a polynucleotide having a nucleotide sequence with ≥90% (preferably ≥95%) homologous to the sequence of SEQ ID NO: 26 and encoding the amino acid sequence of SEQ ID NO: 25;

(d) a polynucleotide complementary to the polynucleotide of any of (a) to (c).

In another preferred embodiment, the nucleic acid molecule comprises a nucleic acid sequence selected from the group consisting of:

(a) a polynucleotide encoding a polypeptide as shown in SEQ ID NOs: 1, 35, 29 or 31;

(b) a polynucleotide having the sequence as shown in SEQ ID NOs: 2, 4, 6, 30 or 32;

(c) a polynucleotide having a nucleotide sequence with ≥95% (preferably ≥98%) homologous to the sequence of SEQ ID NOs: 2, 4, 6, 30 or 32, and encoding the amino acid sequence of SEQ ID NOs: 1, 35, 29 or 31;

(d) a polynucleotide complementary to the polynucleotide of any of (a) to (c).

In another preferred embodiment, the nucleic acid molecule is isolated.

In another preferred embodiment, the nucleic acid molecule further comprises a polynucleotide encoding the leader sequence (directing sequence, signal peptide), and the amino acid sequence of the leader sequence is as shown in SEQ ID NO: 27; preferably the polynucleotide encoding the leader sequence (signal peptide) is as shown in SEQ ID NO: 28.

In another preferred embodiment, the sequence of the nucleic acid molecule is as shown in SEQ ID NOs: 2, 46, 30 or 32.

In a third aspect of the invention, it provides a vector, comprising the nucleic acid molecule of the second aspect of the invention.

In another preferred embodiment, the vector is a lentiviral vector.

In a fourth aspect of the invention, it provides a host cell comprising the vector of the third aspect of the invention or having the exogenous nucleic acid molecule of the second aspect of the invention integrated into its genome.

In another preferred embodiment, the cell is an isolated cell, and/or the cell is a genetically engineered cell.

In another preferred embodiment, the cell is a mammalian cell.

In another preferred embodiment, the cell is a T cell.

In a fifth aspect of the invention, it provides a pharmaceutical composition comprising a pharmaceutically acceptable carrier and the chimeric antigen receptor of the first aspect of the invention, the nucleic acid molecule of the second aspect of the invention, the vector of the third aspect of the invention, or the cell of the fourth aspect of the invention.

In a sixth aspect of the invention, it provides the use of the chimeric antigen receptor of the first aspect of the invention, the nucleic acid molecule of the second aspect of the invention, the vector of the third aspect of the invention, or the cell of the fourth aspect of the invention for the preparation of a medicine or a formulation for treating tumor or autoimmune disease.

In another preferred embodiment, the autoimmune disease is an autoimmune disease caused by overexpression of B cells (such as lupus erythematosus).

In another preferred embodiment, the tumor comprises CD20 positive tumor.

In a seventh aspect of the invention, it provides a method for treating a disease comprising administering an appropriate amount of the chimeric antigen receptor of the first aspect of the invention, the nucleic acid molecule of the second aspect of the invention, the vector of the third aspect of the invention, the cell of the fourth aspect of the invention, or the pharmaceutical composition of the fifth aspect of the invention, to a subject in need of treatment.

In another preferred embodiment, the disease is tumor.

In an eighth aspect of the invention, it provides a method for preparing a CAR-T cell (CAR-modified T cell) expressing the chimeric antigen receptor of the first aspect of the invention, comprising the steps of: transducing the nucleic acid molecule of the second aspect of the invention or the vector of the third aspect of the invention into a T cell, thereby obtaining the CAR-T cell.

It is to be understood that the various technical features of the present invention mentioned above and the various technical features specifically described hereinafter (as in the Examples) may be combined with each other within the scope of the present invention to constitute a new or preferred technical solution, which will not be repeated one by one herein.

MODES FOR CARRYING OUT THE PRESENT INVENTION

Figure 1:
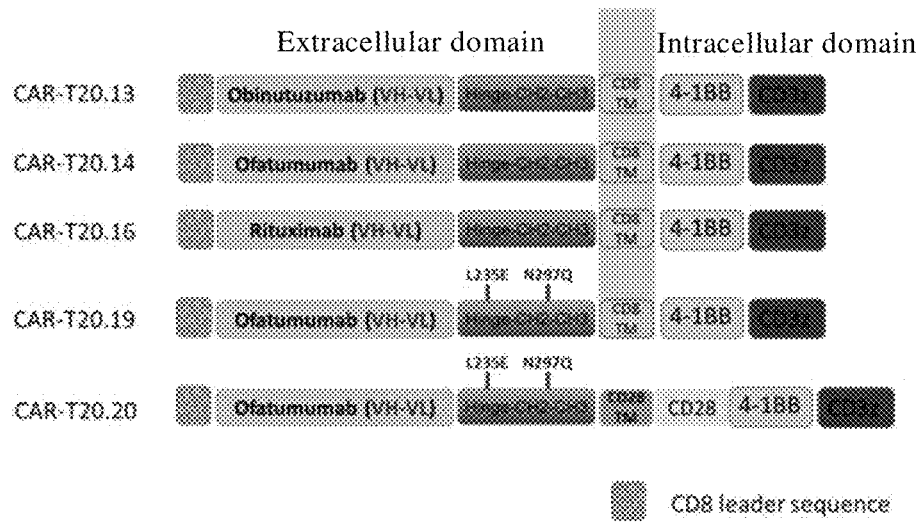
FIG. 1 shows the structure of the chimeric antigen receptor targeting CD20. Each element of the designed CAR structure is shown in the figure, and the listed elements include: a leader sequence, an antigen recognition sequence (Ofatumumaband, Obinutuzumab, Rituximab), a hinge region, a transmembrane region, a co-stimulatory factor signal region, and a CD3ζ signaling region. CAR-T20.14, CAR-T20.13 and CAR-T20.16 are CAR structures constructed based on the antibody variable region sequences of Ofatumumab, Obinutuzumab and Rituxmab, respectively. CAR-T20.19 and CAR-20.20 are the mutant form of CAR-T20.14, having L235E-N297Q mutation in IgG4 Hinge-CH2-CH3 linker region. CAR-T20.20 is a third generation chimeric antigen receptor structure with coding sequences of both CD28 and 4-1BB co-stimulatory signaling molecule.

After extensive and intensive studies, the inventors have obtained a chimeric antigen receptor targeting CD20 and the preparation and application thereof. The extracellular antigen binding domain of the chimeric antigen receptor includes the antibody heavy chain variable region shown in SEQ ID NO: 1 and the antibody light chain variable region shown in SEQ ID NO: 2. The experimental results show that the chimeric antigen receptor provided by the present invention shows extremely high killing ability against tumor cells.

In view of the differences in affinity, killing mechanism of therapeutic antibodies targeting CD20, as well as the significant effects of different transmembrane domains and intracellular domains on the activity of chimeric antigen receptor, a series of chimeric antigen receptors targeting CD20 were constructed in the present invention by combining various transmembrane and intracellular components with the amino acid sequences of the variable regions in various anti-CD20 antibodies. The expression of such chimeric antigen receptors in primary T cells was completed. The detection method of receptor expression intensity was established. The ability of the CAR-T cells to recognize CD20 antigen in vitro and in vivo, as well as the difference in the activity of scavenging malignant tumors carrying CD20 antigen in vitro and in vivo were identified, providing a new effective method and preparation for the clinical application of CAR T in treating CD20 positive leukemia and lymphoma.

Chimeric Antigen Receptor

The invention provides a chimeric antigen receptor (CAR) comprising an extracellular domain, a transmembrane domain, and an intracellular domain. The extracellular domain comprises a target-specific binding element (also known as an antigen binding domain). The intracellular domain includes a co-stimulatory signaling region and a ζ chain moiety. The co-stimulatory signaling region refers to a part of the intracellular domain that includes a co-stimulatory molecule. The co-stimulatory molecule is a cell surface molecule required for efficient response of lymphocytes to antigens, rather than an antigen receptor or its ligand.

A linker can be incorporated between the extracellular domain and the transmembrane domain of the CAR, or between the cytoplasmic domain and the transmembrane domain of the CAR. As used herein, the term "linker" generally refers to any oligopeptide or polypeptide that plays a role of linking the transmembrane domain to the extracellular domain or the cytoplasmic domain in a polypeptide chain. The linker may comprise 0-300 amino acids, preferably 2-100 amino acids and most preferably 3-50 amino acids.

In a preferred embodiment of the invention, the extracellular domain of the CAR provided by the invention comprises an antigen binding domain targeting CD20. When the CAR of the present invention is expressed in T cell, antigen recognition can be performed based on antigen binding specificity. When it binds to its cognate antigen, it affects a tumor cell so that the tumor cell fails to grow, is prompted to die, or otherwise is affected so that the tumor burden in a patient is diminished or eliminated. The antigen binding domain is preferably fused with an intracellular domain from one or more of a co-stimulatory molecule and a ζ chain. Preferably, the antigen binding domain is fused with an intracellular domain of a combination of a 4-1BB signaling domain and/or a CD28 signaling domain, and a CD3ζ signaling domain.

In one embodiment, the CAR targeting CD20 of the invention comprises the specific signaling domain of the invention (the transmembrane region of CD8, the intracellular signal domains of CD137 and CD3ζ are made in series). The signaling domain of the invention significantly increases anti-tumor activity and in vivo persistence of CAR-T cells compared to an otherwise identical CAR targeting CD20.

In a preferred embodiment of the invention, the amino acid sequence of the chimeric antigen receptor (CAR) provided by the present invention is as follows:

```
CAR-T20.13 (SEQ ID NO: 29)
MALPVTALLL PLALLLHAAR PQVQLVQSGA EVKKPGSSVK VSCKASGYAF SYSWINWVRQ    60

APGQGLEWMG RIFPGDGDTD YNGKFKGRVT ITADKSTSTA YMELSSLRSE DTAVYYCARN   120

VFDGYWLVYW GQGTLVTVSS GGGGSGGGGS GGGGSDIVMT QTPLSLPVTP GEPASISCRS   180

SKSLLHSNGI TYLYWYLQKP GQSPQLLIYQ MSNLVSGVPD RFSGSGSGTD FTLKISRVEA   240

EDVGVYYCAQ NLELPYTFGG GTKVEIKRTV ESKYGPPCPP CPAPEFLGGP SVFLFPPKPK   300

DTLMISRTPE VTCVVVDVSQ EDPEVQFNWY VDGVEVHNAK TKPREEQFNS TYRVVSVLTV   360

LHQDWLNGKE YKCKVSNKGL PSSIEKTISK AKGQPREPQV YTLPPSQEEM TKNQVSLTCL   420

VKGFYPSDIA VEWESNGQPE NNYKTTPPVL DSDGSFFLYS RLTVDKSRWQ EGNVFSCSVM   480
```

```
HEALHNHYTQ KSLSLSLGKI YIWAPLAGTC GVLLLSLVIT LYCKRGRKKL LYIFKQPFMR      540

PVQTTQEEDG CSCRFPEEEE GGCELRVKFS RSADAPAYKQ GQNQLYNELN LGRREEYDVL      600

DKRRGRDPEM GGKPRRKNPQ EGLYNELQKD KMAEAYSEIG MKGERRRGKG HDGLYQGLST      660

ATKDTYDALH MQALPPR                                                    677

The DNA sequence encoding CAR-T20.13 (SEQ ID NO: 30)
is as follows:
atggccttac cagtgaccgc cttgctcctg ccgctggcct tgctgctcca cgccgccagg       60
ccgcaggtgc aattggtgca gtctggcgct gaagttaaga agcctgggag ttcagtgaag      120
gtctcctgca aggcttccgg atacgccttc agctattctt ggatcaattg ggtgcggcag      180
gcgcctggac aagggctcga gtggatggga cggatctttc ccggcgatgg ggatactgac      240
tacaatggga aattcaaggg cagagtcaca attaccgccg acaaatccac tagcacagcc      300
tatatggagc tgagcagcct gagatctgag gacacggccg tgtattactg tgcaagaaat      360
gtctttgatg gttactggct tgtttactgg ggccagggaa ccctggtcac cgtctcctca      420
ggtggcggtg gctcgggcgg tggtgggtcg ggtggcggcg gatctgatat cgtgatgacc      480
cagactccac tctccctgcc cgtcacccct ggagagcccg ccagcattag ctgcaggtct      540
agcaagagcc tcttgcacag caatggcatc acttatttgt attggtacct gcaaaagcca      600
gggcagtctc cacagctcct gatttatcaa atgtccaacc ttgtctctgg cgtccctgac      660
cggttctccg gctccgggtc aggcactgat ttcacactga aaatcagcag ggtggaggct      720
gaggatgttg gagtttatta ctgcgctcag aatctagaac ttccttacac cttcggcgga      780
gggaccaagg tggagatcaa acgtacggtg gagagcaagt acggaccgcc ctgcccccct      840
tgccctgccc ccgagttcct gggcggaccc agcgtgttcc tgttcccccc caagcccaag      900 gacacccctga tgatcagccg gacccccgag gtgacctgcg tggtggtgga cgtgagccag      960
gaagatcccg aggtccagtt caattggtac gtggacggcg tggaagtgca caacgccaag     1020
accaagccca gagaggaaca gttcaacagc acctaccggg tggtgtctgt gctgaccgtg     1080
ctgcaccagg actggctgaa cggcaagaa tacaagtgca aggtgtccaa caagggcctg     1140
cccagcagca tcgaaaagac catcagcaag gccaagggcc agcctcgcga gccccaggtg     1200
tacaccctgc ctccctccca ggaagagatg accaagaacc aggtgtccct gacctgcctg     1260
gtgaagggct tctaccccag cgacatcgcc gtggagtggg agagcaacgg ccagcctgag     1320
aacaactaca agaccacccc tcccgtgctg gacagcgacg gcagcttctt cctgtacagc     1380
cggctgaccg tggacaagag ccggtggcag gaaggcaacg tctttagctg cagcgtgatg     1440
cacgaggccc tgcacaacca ctacacccag aagagcctga cctgtccct gggcaagatc     1500 tacatctggg cgcccttggc cgggacttgt ggggtccttc tcctgtcact ggttatcacc     1560
ctttactgca acggggcag aaagaaactc ctgtatatat tcaaacaacc atttatgaga     1620
ccagtacaaa ctactcaaga ggaagatggc tgtagctgcc gatttccaga agaagaagaa     1680
ggaggatgtg aactgagagt gaagttcagc aggagcgcag acgcccccgc gtacaagcag     1740
ggccagaacc agctctataa cgagctcaat ctaggacgaa gagaggagta cgatgttttg     1800
gacaagagac gtggccggga ccctgagatg gggggaaagc cgagaaggaa gaaccctcag     1860
gaaggcctgt acaatgaact gcagaaagat aagatggcgg aggcctacag tgagattggg     1920
atgaaaggcg agcgccggag gggcaagggg cacgatggcc tttaccaggg tctcagtaca     1980
gccaccaagg acacctacga cgcccttcac atgcaggccc tgccccctcg ctag          2034
```

-continued

CAR-T20.14 (SEQ ID NO: 1):
```
MALPVTALLL PLALLLHAAR PEVQLVESGG GLVQPGRSLR LSCAASGFTF NDYAMHWVRQ    60
APGKGLEWVS TISWNSGSIG YADSVKGRFT ISRDNAKKSL YLQMNSLRAE DTALYYCAKD   120
IQYGNYYYGM DVWGQGTTVT VSSGGGGSGG GGSGGGGSEI VLTQSPATLS LSPGERATLS   180
CRASQSVSSY LAWYQQKPGQ APRLLIYDAS NRATGIPARF SGSGSGTDFT LTISSLEPED   240
FAVYYCQQRS NWPITFGQGT RLEIKESKYG PPCPPCPAPE FLGGPSVFLF PPKPKDTLMI   300
SRTPEVTCVV VDVSQEDPEV QFNWYVDGVE VHNAKTKPRE EQFNSTYRVV SVLTVLHQDW   360
LNGKEYKCKV SNKGLPSSIE KTISKAKGQP REPQVYTLPP SQEEMTKNQV SLTCLVKGFY   420
PSDIAVEWES NGQPENNYKT TPPVLDSDGS FFLYSRLTVD KSRWQEGNVF SCSVMHEALH   480
NHYTQKSLSL SLGKIYIWAP LAGTCGVLLL SLVITLYCKR GRKKLLYIFK QPFMRPVQTT   540
QEEDGCSCRF PEEEEGGCEL RVKFSRSADA PAYKQGQNQL YNELNLGRRE EYDVLDKRRG   600
RDPEMGGKPR RKNPQEGLYN ELQKDKMAEA YSEIGMKGER RRGKGHDGLY QGLSTATKDT   660
YDALHMQALP PR                                                      672
```

The DNA sequence encoding CAR-T20.14 (SEQ ID NO: 2) is as follows:
```
atggccttac cagtgaccgc cttgctcctg ccgctggcct tgctgctcca cgccgccagg    60
ccggaagtgc agctggtgga gtctggggga ggcttggtac agcctggcag gtccctgaga   120
ctctcctgtg cagcctctgg attcaccttt aatgattatg ccatgcactg ggtccggcaa   180
gctccaggga agggcctgga gtgggtctca actattagtt ggaatagtgg ttccataggc   240
tatgcggact ctgtgaaggg ccgattcacc atctccagag acaacgccaa gaagtccctg   300
tatctgcaaa tgaacagtct gagagctgag gacacggcct tgtattactg tgcaaaagat   360
atacagtacg gcaactacta ctacggtatg gacgtctggg gccaagggac cacggtcacc   420
gtctcctcag gtggcggtgg ctcgggcggt ggtgggtcgg gtggcggcgg atctgaaatt   480
gtgttgacac agtctccagc caccctgtct ttgtctccag ggaaagagc caccctctcc   540
tgcagggcca gtcagagtgt tagcagctac ttagcctggt accaacagaa acctggccag   600
gctcccaggc tcctcatcta tgatgcatcc aacagggcca ctggcatccc agccaggttc   660
agtggcagtg ggtctgggac agacttcact ctcaccatca gcagcctaga gcctgaagat   720
tttgcagttt attactgtca gcagcgtagc aactggccga tcaccttcgg ccaagggaca   780
cgactggaga ttaagagag caagtacgga ccgccctgcc cccttgccc tgcccccgag   840
ttcctgggcg gacccagcgt gttcctgttc cccccaagc caaggacac cctgatgatc   900
agccggaccc ccgaggtgac ctgcgtggtg gtggacgtga gccaggaaga tcccgaggtc   960
cagttcaatt ggtacgtgga cggcgtggaa gtgcacaacg ccaagaccaa gccagagag  1020
gaacagttca acagcaccta ccgggtggtg tctgtgctga ccgtgctgca ccaggactgg  1080
ctgaacggca agaatacaa gtgcaaggtg tccaacaagg gcctgcccag cagcatcgaa  1140
aagaccatca gcaaggccaa ggccagcct cgcgagcccc aggtgtacac cctgcctccc  1200
tcccaggaag atgaccaa gaaccaggtg tccctgacct gcctggtgaa gggcttctac  1260
cccagcgaca tcgccgtgga gtgggagagc aacggccagc ctgagaacaa ctacaagacc  1320
acccctcccg tgctggacag cgacggcagc ttcttcctgt acagccggct gaccgtggac  1380
aagagccggt ggcaggaagg caacgtcttt agctgcagcg tgatgcacga ggccctgcac  1440
aaccactaca cccagaagag cctgagcctg tccctgggca agatctacat ctgggcgccc  1500
ttggccggga cttgtggggt ccttctcctg tcactggtta tcaccctta ctgcaaacgg  1560
ggcagaaaga aactcctgta tatattcaaa caaccattta tgagaccagt acaaactact  1620
```

-continued

```
caagaggaag atggctgtag ctgccgattt ccagaagaag aagaaggagg atgtgaactg    1680
agagtgaagt tcagcaggag cgcagacgcc cccgcgtaca agcagggcca gaaccagctc    1740
tataacgagc tcaatctagg acgaagagag gagtacgatg ttttggacaa gagacgtggc    1800
cgggaccctg agatggggg aaagccgaga aggaagaacc ctcaggaagg cctgtacaat     1860
gaactgcaga aagataagat ggcggaggcc tacagtgaga ttgggatgaa aggcgagcgc    1920
cggaggggca aggggcacga tggcctttac cagggtctca gtacagccac caaggacacc    1980
tacgacgccc ttcacatgca ggccctgccc cctcgctag                           2019
```

CAR-T20.16 (SEQ ID NO: 3)

```
MALPVTALLL PLALLLHAAR PQVQLQQPGA ELVKPGASVK MSCKASGYTF TSYNMHWVKQ     60

TPGRGLEWIG AIYPGNGDTS YNQKFKGKAT LTADKSSSTA YMQLSSLTSE DSAVYYCARS    120

TYYGGDWYFN VWGAGTTVTV SAGGGGSGGG GSGGGGSQIV LSQSPAILSA SPGEKVTMTC    180

RASSSVSYIH WFQQKPGSSP KPWIYATSNL ASGVPVRFSG SGSGTSYSLT ISRVEAEDAA    240

TYYCQQWTSN PPTFGGGTKL EIKESKYGPP CPPCPAPEFL GGPSVFLFPP KPKDTLMISR    300

TPEVTCVVVD VSQEDPEVQF NWYVDGVEVH NAKTKPREEQ FNSTYRVVSV LTVLHQDWLN    360

GKEYKCKVSN KGLPSSIEKT ISKAKGQPRE PQVYTLPPSQ EEMTKNQVSL TCLVKGFYPS    420

DIAVEWESNG QPENNYKTTP PVLDSDGSFF LYSRLTVDKS RWQEGNVFSC SVMHEALHNH    480

YTQKSLSLSL GKIYIWAPLA GTCGVLLLSL VITLYCKRGR KKLLYIFKQP FMRPVQTTQE    540

EDGCSCRFPE EEEGGCELRV KFSRSADAPA YKQGQNQLYN ELNLGRREEY DVLDKRRGRD    600

PEMGGKPRRK NPQEGLYNEL QKDKMAEAYS EIGMKGERRR GKGHDGLYQG LSTATKDTYD    660

ALHMQALPPR                                                          670
```

The DNA sequence encoding CAR-T20.16 (SEQ ID NO: 4)
is as follows:

```
ATGGCCTTAC CAGTGACCGC CTTGCTCCTG CCGCTGGCCT TGCTGCTCCA CGCCGCCAGG     60

CCGCAGGTGC AGTTGCAACA GCCTGGAGCT GAGTTGGTGA AGCCTGGTGC TTCTGTGAAG    120

ATGTCTTGTA AGGCTTCTGG ATACACATTC ACTTCTTACA ACATGCACTG GGTGAAGCAG    180

ACTCCTGGTA GGGGTTTGGA GTGGATCGGA GCTATCTACC CAGGAAACGG AGACACATCT    240

TACAACCAGA AGTTCAAGGG TAAGGCTACA TTGACTGCTG ACAAGTCTTC ATCTACTGCT    300

TACATGCAAT TGTCTTCTTT GACATCTGAG GACTCTGCAG TTTACTACTG CGCTAGGTCT    360

ACATACTACG GAGGTGACTG GTACTTCAAC GTGTGGGGAG CAGGTACCAC GGTCACTGTC    420

TCTGCAGGTG GAGGTGGATC TGGAGGAGGA GGATCTGGTG GAGGAGGTTC TCAAATTGTT    480

CTCTCCCAGT CTCCAGCAAT CCTGTCAGCT TCTCCTGGAG AGAAGGTGAC TATGACTTGC    540

AGGGCTTCTT CATCTGTTTC TTACATCCAC TGGTTCCAGC AGAAGCCTGG TTCTTCACCT    600

AAGCCTTGGA TCTACGCTAC ATCTAACTTG GCATCTGGAG TGCCTGTGAG GTTCTCTGGT    660

TCTGGTTCAG GTACTTCTTA CTCTTTGACA ATCTCTAGGG TGGAGGCTGA GGACGCTGCT    720

ACTTACTACT GCCAGCAGTG GACATCTAAC CCTCCAACAT TCGGAGGTGG TACTAAGTTG    780

GAGATCAAGG AGAGCAAGTA CGGACCGCCC TGCCCCCCTT GCCCTGCCCC CGAGTTCCTG    840

GGCGGACCCA GCGTGTTCCT GTTCCCCCCC AAGCCCAAGG ACACCCTGAT GATCAGCCGG    900

ACCCCCGAGG TGACCTGCGT GGTGGTGGAC GTGAGCCAGG AAGATCCCGA GGTCCAGTTC    960

AATTGGTACG TGGACGGCGT GGAAGTGCAC AACGCCAAGA CCAAGCCCAG AGAGGAACAG   1020

TTCAACAGCA CCTACCGGGT GGTGTCTGTG CTGACCGTGC TGCACCAGGA CTGGCTGAAC   1080

GGCAAAGAAT ACAAGTGCAA GGTGTCCAAC AAGGGCCTGC CCAGCAGCAT CGAAAAGACC   1140

ATCAGCAAGG CCAAGGGCCA GCCTCGCGAG CCCCAGGTGT ACACCCTGCC TCCCTCCCAG   1200
```

-continued

```
GAAGAGATGA CCAAGAACCA GGTGTCCCTG ACCTGCCTGG TGAAGGGCTT CTACCCCAGC   1260

GACATCGCCG TGGAGTGGGA GAGCAACGGC CAGCCTGAGA ACAACTACAA GACCACCCCT   1320

CCCGTGCTGG ACAGCGACGG CAGCTTCTTC CTGTACAGCC GGCTGACCGT GGACAAGAGC   1380

CGGTGGCAGG AAGGCAACGT CTTTAGCTGC AGCGTGATGC ACGAGGCCCT GCACAACCAC   1440

TACACCCAGA AGAGCCTGAG CCTGTCCCTG GGCAAGATCT ACATCTGGGC GCCCTTGGCC   1500

GGGACTTGTG GGGTCCTTCT CCTGTCACTG GTTATCACCC TTTACTGCAA ACGGGGCAGA   1560

AAGAAACTCC TGTATATATT CAAACAACCA TTTATGAGAC CAGTACAAAC TACTCAAGAG   1620

GAAGATGGCT GTAGCTGCCG ATTTCCAGAA GAAGAAGAAG GAGGATGTGA ACTGAGAGTG   1680

AAGTTCAGCA GGAGCGCAGA CGCCCCCGCG TACAAGCAGG GCCAGAACCA GCTCTATAAC   1740

GAGCTCAATC TAGGACGAAG AGAGGAGTAC GATGTTTTGG ACAAGAGACG TGGCCGGGAC   1800

CCTGAGATGG GGGGAAAGCC GAGAAGGAAG AACCCTCAGG AAGGCCTGTA CAATGAACTG   1860

CAGAAAGATA AGATGGCGGA GGCCTACAGT GAGATTGGGA TGAAAGGCGA GCGCCGGAGG   1920

GGCAAGGGGC ACGATGGCCT TTACCAGGGT CTCAGTACAG CCACCAAGGA CACCTACGAC   1980

GCCCTTCACA TGCAGGCCCT GCCCCCTCGC TAG                               2013
```

In another more preferred embodiment of the invention, the amino acid sequence of the chimeric antigen receptor (CAR) provided by the invention is as follows:

```
CAR-T20.19
                                                      (SEQ ID NO: 5)
MALPVTALLL PLALLLHAAR PEVQLVESGG GLVQPGRSLR LSCAASGFTF NDYAMHWVRQ    60

APGKGLEWVS TISWNSGSIG YADSVKGRFT ISRDNAKKSL YLQMNSLRAE DTALYYCAKD   120

IQYGNYYYGM DVWGQGTTVT VSSGGGGSGG GGSGGGGSEI VLTQSPATLS LSPGERATLS   180

CRASQSVSSY LAWYQQKPGQ APRLLIYDAS NRATGIPARF SGSGSGTDFT LTISSLEPED   240

FAVYYCQQRS NWPITFGQGT RLEIKESKYG PPCPPCPAPE FEGGPSVFLF PPKPKDTLMI   300

SRTPEVTCVV VDVSQEDPEV QFNWYVDGVE VHNAKTKPRE EQFQSTYRVV SVLTVLHQDW   360

LNGKEYKCKV SNKGLPSSIE KTISKAKGQP REPQVYTLPP SQEEMTKNQV SLTCLVKGFY   420

PSDIAVEWES NGQPENNYKT TPPVLDSDGS FFLYSRLTVD KSRWQEGNVF SCSVMHEALH   480

NHYTQKSLSL SLGKIYIWAP LAGTCGVLLL SLVITLYCKR GRKKLLYIFK QPFMRPVQTT   540

QEEDGCSCRF PEEEEGGCEL RVKFSRSADA PAYKQGQNQL YNELNLGRRE EYDVLDKRRG   600

RDPEMGGKPR RKNPQEGLYN ELQKDKMAEA YSEIGMKGER RRGKGHDGLY QGLSTATKDT   660

YDALHMQALP PR                                                      672
```

The DNA sequence encoding CAR-T20.19 is as follows:

```
                                                      (SEQ ID NO: 6)
atggccttac cagtgaccgc cttgctcctg ccgctggcct tgctgctcca cgccgccagg    60
ccggaagtgc agctggtgga gtctggggga ggcttggtac agcctggcag gtccctgaga   120
ctctcctgtg cagcctctgg attcaccttt aatgattatg ccatgcactg ggtccggcaa   180
gctccaggga agggcctgga gtgggtctca actattagtt ggaatagtgg ttccataggc   240
tatgcggact ctgtgaaggg ccgattcacc atctccagag acaacgccaa gaagtccctg   300
tatctgcaaa tgaacagtct gagagctgag gacacggcct tgtattactg tgcaaaagat   360
atacagtacg gcaactacta ctacggtatg gacgtctggg gccaagggac cacggtcacc   420
gtctcctcag gtggcggtgg ctcgggcggt ggtgggtcgg gtggcggcgg atctgaaatt   480
gtgttgacac agtctccagc caccctgtct ttgtctccag gggaaagagc caccctctcc   540
```

-continued

```
tgcagggcca gtcagagtgt tagcagctac ttagcctggt accaacagaa acctggccag    600
gctcccaggc tcctcatcta tgatgcatcc aacagggcca ctggcatccc agccaggttc    660
agtggcagtg ggtctgggac agacttcact ctcaccatca gcagcctaga gcctgaagat    720
tttgcagttt attactgtca gcagcgtagc aactggccga tcaccttcgg ccaagggaca    780
cgactggaga ttaaagagag caagtacgga ccgccctgcc ccccttgccc tgccccgag    840 ttcgagggcg gacccagcgt gttcctgttc ccccccaagc caaggacac cctgatgatc    900 agccggaccc ccgaggtgac ctgcgtggtg gtggacgtga gccaggaaga tcccgaggtc    960
cagttcaatt ggtacgtgga cggcgtggaa gtgcacaacg ccaagaccaa gcccagagag   1020
gaacagttcc aaagcaccta ccgggtggtg tctgtgctga ccgtgctgca ccaggactgg   1080
ctgaacggca agaatacaa gtgcaaggtg tccaacaagg gcctgcccag cagcatcgaa   1140
aagaccatca gcaaggccaa gggccagcct cgcgagcccc aggtgtacac cctgcctccc   1200
tcccaggaag agatgaccaa gaaccaggtg tccctgacct gcctggtgaa gggcttctac   1260
cccagcgaca tcgccgtgga gtgggagagc aacggccagc ctgagaacaa ctacaagacc   1320
accccctccg tgctggacag cgacggcagc ttcttcctgt acagccggct gaccgtggac   1380
aagagccggt ggcaggaagg caacgtcttt agctgcagcg tgatgcacga ggccctgcac   1440
aaccactaca cccagaagag cctgagcctg tccctgggca gatctacat ctgggcgccc   1500 ttggccggga cttgtggggt ccttctcctg tcactggtta tcacccttta ctgcaaacgg   1560
ggcagaaaga aactcctgta tatattcaaa caaccattta tgagaccagt acaaactact   1620
caagaggaag atggctgtag ctgccgattt ccagaagaag aagaaggagg atgtgaactg   1680
agagtgaagt tcagcaggag cgcagacgcc cccgcgtaca gcagggcca gaaccagctc   1740 tataacgagc tcaatctagg acgaagagag gagtacgatg ttttggacaa gagacgtggc   1800
cgggaccctg agatgggggg aaagccgaga aggaagaacc ctcaggaagg cctgtacaat   1860
gaactgcaga aagataagat ggcggaggcc tacagtgaga ttgggatgaa aggcgagcgc   1920
cggaggggca aggggcacga tggcctttac cagggtctca gtacagccac caaggacacc   1980
tacgacgccc ttcacatgca ggccctgccc cctcgctag                          2019
```

In another most preferred embodiment of the invention, the amino acid sequence of the chimeric antigen receptor (CAR) provided by the invention is as follows:

```
CAR-T20.20
                                                     (SEQ ID NO: 31)
MALPVTALLL PLALLLHAAR PEVQLVESGG GLVQPGRSLR LSCAASGFTF NDYAMHWVRQ     60

APGKGLEWVS TISWNSGSIG YADSVKGRFT ISRDNAKKSL YLQMNSLRAE DTALYYCAKD    120

IQYGNYYYGM DVWGQGTTVT VSSGGGGSGG GGSGGGGSEI VLTQSPATLS LSPGERATLS    180

CRASQSVSSY LAWYQQKPGQ APRLLIYDAS NRATGIPARF SGSGSGTDFT LTISSLEPED    240

FAVYYCQQRS NWPITFGQGT RLEIKESKYG PPCPPCPAPE FEGGPSVFLF PPKPKDTLMI    300

SRTPEVTCVV VDVSQEDPEV QFNWYVDGVE VHNAKTKPRE EQFQSTYRVV SVLTVLHQDW    360

LNGKEYKCKV SNKGLPSSIE KTISKAKGQP REPQVYTLPP SQEEMTKNQV SLTCLVKGFY    420

PSDIAVEWES NGQPENNYKT TPPVLDSDGS FFLYSRLTVD KSRWQEGNVF SCSVMHEALH    480

NHYTQKSLSL SLGKFWVLVV VGGVLACYSL LVTVAFIIFW VRSKRSRLLH SDYMNMTPRR    540

PGPTRKHYQP YAPPRDFAAY RSKRGRKKLL YIFKQPFMRP VQTTQEEDGC SCRFPEEEEG    600
```

```
GCELRVKFSR SADAPAYKQG QNQLYNELNL GRREEYDVLD KRRGRDPEMG GKPRRKNPQE    660

GLYNELQKDK MAEAYSEIGM KGERRRGKGH DGLYQGLSTA TKDTYDALHM QALPPR        716
```

The coding DNA sequence of CAR-T20.20 is as follows:

(SEQ ID NO: 32)

```
atggcttac cagtgaccgc cttgctcctg ccgctggcct tgctgctcca cgccgccagg      60
ccggaagtgc agctggtgga gtctggggga ggcttggtac agcctggcag gtccctgaga   120
ctctcctgtg cagcctctgg attcaccttt aatgattatg ccatgcactg ggtccggcaa   180
gctccaggga agggcctgga gtgggtctca actattagtt ggaatagtgg ttccataggc   240
tatgcggact ctgtgaaggg ccgattcacc atctccagag acaacgccaa gaagtccctg   300
tatctgcaaa tgaacagtct gagagctgag gacacggcct tgtattactg tgcaaaagat   360
atacagtacg gcaactacta ctacggtatg gacgtctggg gccaagggac cacggtcacc   420
gtctcctcag gtggcggtgg ctcgggcggt ggtgggtcgg gtggcggcgg atctgaaatt   480
gtgttgacac agtctccagc caccctgtct ttgtctccag gggaaagagc caccctctcc   540
tgcagggcca gtcagagtgt tagcagctac ttagcctggt accaacagaa acctggccag   600
gctcccaggc tcctcatcta tgatgcatcc aacagggcca ctggcatccc agccaggttc   660
agtggcagtg ggtctgggac agacttcact ctcaccatca gcagcctaga gcctgaagat   720
tttgcagttt attactgtca gcagcgtagc aactggccga tcaccttcgg ccaagggaca   780
cgactggaga ttaagagag caagtacgga ccgccctgcc cccttgccc tgccccgag    840
ttcgagggcg acccagcgt gttcctgttc ccccccaagc caaggacac cctgatgatc    900
agccggaccc ccgaggtgac ctgcgtggtg gtggacgtga gccaggaaga tcccgaggtc   960
cagttcaatt ggtacgtgga cggcgtggaa gtgcacaacg ccaagaccaa gcccagagag  1020
gaacagttcc aaagcaccta ccgggtggtg tctgtgctga ccgtgctgca ccaggactgg  1080
ctgaacggca agaatacaa gtgcaaggtg tccaacaagg gcctgcccag cagcatcgaa  1140
aagaccatca gcaaggccaa gggccagcct cgcgagcccc aggtgtacac cctgcctccc  1200
tcccaggaag agatgaccaa gaaccaggtg tccctgacct gcctggtgaa gggcttctac  1260
cccagcgaca tcgccgtgga gtgggagagc aacggccagc ctgagaacaa ctacaagacc  1320
accccctccg tgctggacag cgacggcagc ttcttcctgt acagccggct gaccgtggac  1380
aagagccggt ggcaggaagg caacgtcttt agctgcagcg tgatgcacga ggccctgcac  1440
aaccactaca cccagaagag cctgagcctg tccctgggca gttttgggt gctggtggtg  1500
gttggtggag tcctggcttg ctatagcttg ctagtaacag tggcctttat tattttctgg  1560
gtgaggagta agaggagcag gctcctgcac agtgactaca tgaacatgac tccccgccgc  1620
cccgggccca cccgcaagca ttaccagccc tatgccccac cacgcgactt cgcagcctat  1680
cgctccaaac ggggcagaaa gaaactcctg tatatattca acaaccatt tatgagacca  1740
gtacaaacta ctcaagagga agatggctgt agctgccgat tccagaaga agaagaagga  1800
ggatgtgaac tgagagtgaa gttcagcagg agcgcagacg cccccgcgta caagcagggc  1860
cagaaccagc tctataacga gctcaatcta ggacgaagag aggagtacga tgttttggac  1920
aagagacgtg gccgggaccc tgagatgggg ggaaagccga aggaagaa ccctcaggaa  1980
ggcctgtaca atgaactgca gaaagataag atggcggagg cctacagtga gattgggatg  2040
aaaggcgagc gccggaggggg caaggggcac gatggccttt accagggtct cagtacagcc  2100
accaaggaca cctacgacgc ccttcacatg caggccctgc cccctcgcta a           2151
```

Antigen Binding Domain

In one embodiment, the CAR of the invention comprises a target-specific binding element referred to as antigen binding domain. The antigen binding domain of the CAR of the invention is a specific binding element targeting CD20.

In a preferred embodiment of the invention, the antigen binding domain comprises a heavy chain variable region and a light chain variable region of an anti-CD20 antibody.

In another preferred embodiment, the amino acid sequence of the heavy chain variable region of Ofatumumaband antibody is as follows:

```
                                                          (SEQ ID NO: 7)
EVQLVESGGG LVQPGRSLRL SCAASGFTFN DYAMHWVRQA PGKGLEWVST ISWNSGSIGY    60

ADSVKGRFTI SRDNAKKSLY LQMNSLRAED TALYYCAKDI QYGNYYYGMD VWGQGTTVTV   120

SS;                                                                122
``` and the DNA sequence encoding the heavy chain variable region of Ofatumumaband antibody is as follows:

```
                                                          (SEQ ID NO: 8)
GAAGTGCAGC TGGTGGAGTC TGGGGGAGGC TTGGTACAGC CTGGCAGGTC CCTGAGACTC    60

TCCTGTGCAG CCTCTGGATT CACCTTTAAT GATTATGCCA TGCACTGGGT CCGGCAAGCT   120

CCAGGGAAGG GCCTGGAGTG GGTCTCAACT ATTAGTTGGA ATAGTGGTTC CATAGGCTAT   180

GCGGACTCTG TGAAGGGCCG ATTCACCATC TCCAGAGACA ACGCCAAGAA GTCCCTGTAT   240

CTGCAAATGA ACAGTCTGAG AGCTGAGGAC ACGGCCTTGT ATTACTGTGC AAAAGATATA   300

CAGTACGGCA ACTACTACTA CGGTATGGAC GTCTGGGGCC AAGGGACCAC GGTCACCGTC   360

TCCTCA;                                                            366
``` or, the amino acid sequence of the heavy chain variable region of Rituximab antibody is as follows:

```
                                                          (SEQ ID NO: 9)
QVQLQQPGAE LVKPGASVKM SCKASGYTFT SYNMHWVKQT PGRGLEWIGA IYPGNGDTSY    60

NQKFKGKATL TADKSSSTAY MQLSSLTSED SAVYYCARST YYGGDWYFNV WGAGTTVTVS   120

A;                                                                 121
``` and the DNA sequence encoding the heavy chain variable region of Rituximab antibody is as follows:

```
                                                          (SEQ ID NO: 10)
CAGGTGCAGT TGCAACAGCC TGGAGCTGAG TTGGTGAAGC CTGGTGCTTC TGTGAAGATG    60

TCTTGTAAGG CTTCTGGATA CACATTCACT TCTTACAACA TGCACTGGGT GAAGCAGACT   120

CCTGGTAGGG GTTTGGAGTG GATCGGAGCT ATCTACCCAG GAAACGGAGA CACATCTTAC   180

AACCAGAAGT TCAAGGGTAA GGCTACATTG ACTGCTGACA AGTCTTCATC TACTGCTTAC   240

ATGCAATTGT CTTCTTTGAC ATCTGAGGAC TCTGCAGTTT ACTACTGCGC TAGGTCTACA   300

TACTACGGAG GTGACTGGTA CTTCAACGTG TGGGGAGCAG GTACCACGGT CACTGTCTCT   360

GCA.                                                               363
```

Further, the amino acid sequence of the heavy chain variable region of Obinutuzumab antibody used in the present invention is as follows:

```
                                                      (SEQ ID NO: 33)
QVQLVQSGAE VKKPGSSVKV SCKASGYAFS YSWINWVRQA PGQGLEWMGR IFPGDGDTDY   60

NGKFKGRVTI TADKSTSTAY MELSSLRSED TAVYYCARNV FDGYWLVYWG QGTLVTVSS   119
```

The DNA sequence encoding the heavy chain variable region of Obinutuzumab antibody is as follows:

```
                                                      (SEQ ID NO: 34)
caggtgcaat tggtgcagtc tggcgctgaa gttaagaagc ctgggagttc agtgaaggtc   60
tcctgcaagg cttccggata cgccttcagc tattcttgga tcaattgggt gcggcaggcg  120
cctggacaag ggctcgagtg gatgggacgg atctttcccg gcgatgggga tactgactac  180
aatgggaaat tcaagggcag agtcacaatt accgccgaca atccactag cacagcctat   240 atggagctga gcagcctgag atctgaggac acggccgtgt attactgtgc aagaaatgtc  300
tttgatggtt actggcttgt ttactggggc cagggaaccc tggtcaccgt ctcctca     357
```

In another preferred embodiment, the amino acid sequence of the light chain variable region of Ofatumumaband antibody is as follows:

```
                                                      (SEQ ID NO: 11)
EIVLTQSPAT LSLSPGERAT LSCRASQSVS SYLAWYQQKP GQAPRLLIYD ASNRATGIPA   60

RFSGSGSGTD FTLTISSLEP EDFAVYYCQQ RSNWPITFGQ GTRLEIK               107
```

The DNA sequence of Ofatumumaband antibody is as follows:

```
                                                      (SEQ ID NO: 12)
GAAATTGTGT TGACACAGTC TCCAGCCACC CTGTCTTTGT CTCCAGGGGA AAGAGCCACC   60

CTCTCCTGCA GGGCCAGTCA GAGTGTTAGC AGCTACTTAG CCTGGTACCA ACAGAAACCT  120

GGCCAGGCTC CCAGGCTCCT CATCTATGAT GCATCCAACA GGGCCACTGG CATCCCAGCC  180

AGGTTCAGTG GCAGTGGGTC TGGGACAGAC TTCACTCTCA CCATCAGCAG CCTAGAGCCT  240

GAAGATTTTG CAGTTTATTA CTGTCAGCAG CGTAGCAACT GGCCGATCAC CTTCGGCCAA  300

GGGACACGAC TGGAGATTAA A                                           321
```

Alternatively, the amino acid sequence of the light chain variable region of Rituximab antibody is as follows:

```
                                                      (SEQ ID NO: 13)
QIVLSQSPAI LSASPGEKVT MTCRASSSVS YIHWFQQKPG SSPKPWIYAT SNLASGVPVR   60

FSGSGSGTSY SLTISRVEAE DAATYYCQQW TSNPPTFGGG TKLEIK                106
```

The DNA sequences encoding the light chain (VL) of single-chain variable region derived from Rituximab antibody is:

```
                                                      (SEQ ID NO: 14)
CAAATTGTTC TCTCCCAGTC TCCAGCAATC CTGTCAGCTT CTCCTGGAGA GAAGGTGACT   60

ATGACTTGCA GGGCTTCTTC ATCTGTTTCT TACATCCACT GGTTCCAGCA GAAGCCTGGT  120

TCTTCACCTA AGCCTTGGAT CTACGCTACA TCTAACTTGG CATCTGGAGT GCCTGTGAGG  180
```

```
TTCTCTGGTT CTGGTTCAGG TACTTCTTAC TCTTTGACAA TCTCTAGGGT GGAGGCTGAG    240

GACGCTGCTA CTTACTACTG CCAGCAGTGG ACATCTAACC CTCCAACATT CGGAGGTGGT    300

ACTAAGTTGG AGATCAAG.                                                 318
```

Further, the amino acid sequence of the light chain variable region of Obinutuzumab antibody used in the present invention is as follows:

```
                                                      (SEQ ID NO: 35)
DIVMTQTPLS LPVTPGEPAS ISCRSSKSLL HSNGITYLYW YLQKPGQSPQ LLIYQMSNLV     60

SGVPDRFSGS GSGTDFTLKI SRVEAEDVGV YYCAQNLELP YTFGGGTKVE IKRTV        115
```

The DNA sequence encoding the heavy chain variable region of Obinutuzumab antibody is as follows:

```
                                                      (SEQ ID NO: 36)
gatatcgtga tgacccagac tccactctcc ctgcccgtca ccccctggaga gcccgccagc    60 attagctgca ggtctagcaa gagcctcttg cacagcaatg gcatcactta tttgtattgg   120
tacctgcaaa agccagggca gtctccacag ctcctgattt atcaaatgtc caaccttgtc   180
tctggcgtcc ctgaccggtt ctccggctcc gggtcaggca ctgatttcac actgaaaatc   240
agcagggtgg aggctgagga tgttggagtt tattactgcg ctcagaatct agaacttcct   300
tacaccttcg gcggagggac caaggtggag atcaaacgta cggtg                   345
```

In a preferred embodiment of the invention, the amino acid sequence of the linker between the heavy chain variable region and the light chain variable region is as follows:

```
                  (SEQ ID NO: 15)
     GGGGSGGGGS GGGGS         15
``` and its coding DNA sequence is as follows:

```
                                (SEQ ID NO: 16)
GGTGGCGGTG GCTCGGGCGG TGGTGGGTCG GGTGGCGGCG    45

GATCT                                          45
```

Hinge Region and Transmembrane Region

As for the hinge region and the transmembrane region (transmembrane domain), the CAR can be designed to comprise a transmembrane domain fused to the extracellular domain of the CAR. In one embodiment, a transmembrane domain that is naturally associated with one of the domains in the CAR is used. In some embodiments, transmembrane domains may be selected or modified by amino acid substitutions to avoid binding such domains to the transmembrane domain of the same or different surface membrane proteins, thereby minimizing the interaction with other members of the receptor complexes.

In a preferred embodiment of the invention, the hinge region comprises the following amino acid sequence (IgG4 Hinge-CH2-CH3 hinge region):

```
                                                      (SEQ ID NO: 17)
ESKYGPPCPP CPAPEFLGGP SVFLFPPKPK DTLMISRTPE VTCVVVDVSQ EDPEVQFNWY     60

VDGVEVHNAK TKPREEQFNS TYRVVSVLTV LHQDWLNGKE YKCKVSNKGL PSSIEKTISK   120
```

AKGQPREPQV YTLPPSQEEM TKNQVSLTCL VKGFYPSDIA VEWESNGQPE NNYKTTPPVL 180

DSDGSFFLYS RLTVDKSRWQ EGNVFSCSVM HEALHNHYTQ KSLSLSLGK 229

Its coding DNA sequence is as follows:

(SEQ ID NO: 18)
GAGAGCAAGT ACGGACCGCC CTGCCCCCCT TGCCCTGCCC CCGAGTTCCT GGGCGGACCC 60

AGCGTGTTCC TGTTCCCCCC CAAGCCCAAG GACACCCTGA TGATCAGCCG GACCCCCGAG 120

GTGACCTGCG TGGTGGTGGA CGTGAGCCAG GAAGATCCCG AGGTCCAGTT CAATTGGTAC 180

GTGGACGGCG TGGAAGTGCA CAACGCCAAG ACCAAGCCCA GAGAGGAACA GTTCAACAGC 240

ACCTACCGGG TGGTGTCTGT GCTGACCGTG CTGCACCAGG ACTGGCTGAA CGGCAAAGAA 300

TACAAGTGCA AGGTGTCCAA CAAGGGCCTG CCCAGCAGCA TCGAAAAGAC CATCAGCAAG 360

GCCAAGGGCC AGCCTCGCGA GCCCCAGGTG TACACCCTGC CTCCCTCCCA GGAAGAGATG 420

ACCAAGAACC AGGTGTCCCT GACCTGCCTG GTGAAGGGCT TCTACCCCAG CGACATCGCC 480

GTGGAGTGGG AGAGCAACGG CCAGCCTGAG AACAACTACA AGACCACCCC TCCCGTGCTG 540

GACAGCGACG GCAGCTTCTT CCTGTACAGC CGGCTGACCG TGGACAAGAG CCGGTGGCAG 600

GAAGGCAACG TCTTTAGCTG CAGCGTGATG CACGAGGCCC TGCACAACCA CTACACCCAG 660

AAGAGCCTGA GCCTGTCCCT GGGCAAG; 687 or, the hinge region comprises the following amino acid
sequence (IgG4 Hinge-CH2-CH3 (L235E, N297Q)):

(SEQ ID NO: 19)
ESKYGPPCPP CPAPEFEGGP SVFLFPPKPK DTLMISRTPE VTCVVVDVSQ EDPEVQFNWY 60

VDGVEVHNAK TKPREEQFQS TYRVVSVLTV LHQDWLNGKE YKCKVSNKGL PSSIEKTISK 120

AKGQPREPQV YTLPPSQEEM TKNQVSLTCL VKGFYPSDIA VEWESNGQPE NNYKTTPPVL 180

DSDGSFFLYS RLTVDKSRWQ EGNVFSCSVM HEALHNHYTQ KSLSLSLGK 229

Its coding DNA sequence is as follows:

(SEQ ID NO: 20)
GAGAGCAAGT ACGGACCGCC CTGCCCCCCT TGCCCTGCCC CCGAGTTCGA GGGCGGACCC 60

AGCGTGTTCC TGTTCCCCCC CAAGCCCAAG GACACCCTGA TGATCAGCCG GACCCCCGAG 120

GTGACCTGCG TGGTGGTGGA CGTGAGCCAG GAAGATCCCG AGGTCCAGTT CAATTGGTAC 180

GTGGACGGCG TGGAAGTGCA CAACGCCAAG ACCAAGCCCA GAGAGGAACA GTTCCAAAGC 240

ACCTACCGGG TGGTGTCTGT GCTGACCGTG CTGCACCAGG ACTGGCTGAA CGGCAAAGAA 300

TACAAGTGCA AGGTGTCCAA CAAGGGCCTG CCCAGCAGCA TCGAAAAGAC CATCAGCAAG 360

GCCAAGGGCC AGCCTCGCGA GCCCCAGGTG TACACCCTGC CTCCCTCCCA GGAAGAGATG 420

ACCAAGAACC AGGTGTCCCT GACCTGCCTG GTGAAGGGCT TCTACCCCAG CGACATCGCC 480

GTGGAGTGGG AGAGCAACGG CCAGCCTGAG AACAACTACA AGACCACCCC TCCCGTGCTG 540

GACAGCGACG GCAGCTTCTT CCTGTACAGC CGGCTGACCG TGGACAAGAG CCGGTGGCAG 600

GAAGGCAACG TCTTTAGCTG CAGCGTGATG CACGAGGCCC TGCACAACCA CTACACCCAG 660

AAGAGCCTGA GCCTGTCCCT GGGCAAG. 687

In a preferred embodiment of the invention, the amino acid sequence of the transmembrane region derived from CD8 (CD8TM) is as follows:

```
                              (SEQ ID NO: 21)
     IYIWAPLAGT CGVLLLSLVI TLYC          24
```

The coding DNA sequence thereof is as follows:

```
                                                  (SEQ ID NO: 22)
ATCTACATCT GGGCGCCCTT GGCCGGGACT TGTGGGGTCC TTCTCCTGTC ACTGGTTATC  60

ACCCTTTACT GC                                                     72
```

In a preferred embodiment of the invention, the amino acid sequence of the transmembrane region derived from CD28 (CD28TM) is as follows:

```
                              (SEQ ID NO: 37)
     FWVLVVVGGV LACYSLLVTV AFIIFWV;        27
```

The DNA sequence encoding the transmembrane region derived from CD28 (CD28TM) is as follows:

```
                                                  (SEQ ID NO: 38)
TTTTGGGTGC TGGTGGTGGT TGGTGGAGTC CTGGCTTGCT ATAGCTTGCT AGTAACAGTG  60

GCCTTTATTA TTTTCTGGGT G.                                          81
```

Intracellular Domain

The intracellular domain in the CAR of the invention comprises the signaling domain of 4-1BB and the signaling domain of CD3ζ.

Preferably, the intracellular signaling domain of 4-1BB comprises the following amino acid sequence:

```
                              (SEQ ID NO: 23)
KRGRKKLLYI FKQPFMRPVQ TTQEEDGCSC RFPEEEEGGC EL      42
```

The coding DNA sequence thereof is as follows:

```
                                                  (SEQ ID NO: 24)
AAACGGGGCA GAAAGAAACT CCTGTATATA TTCAAACAAC CATTTATGAG ACCAGTACAA   60

ACTACTCAAG AGGAAGATGG CTGTAGCTGC CGATTTCCAG AAGAAGAAGA AGGAGGATGT  120

GAACTG                                                            126
```

Preferably, the intracellular signaling domain derived from CD28 comprises the following amino acid sequence:

```
                              (SEQ ID NO: 39)
RSKRSRLLHS DYMNMTPRRP GPTRKHYQPY APPRDFAAYR S      41
```

The coding DNA sequence thereof is as follows:

```
                                                  (SEQ ID NO: 40)
AGGAGTAAGA GGAGCAGGCT CCTGCACAGT GACTACATGA ACATGACTCC CCGCCGCCCC   60

GGGCCCACCC GCAAGCATTA CCAGCCCTAT GCCCCACCAC GCGACTTCGC AGCCTATCGC  120

TCC                                                               123
```

Preferably, the intracellular signaling domain of CD3ζ comprises the following amino acid sequence:

```
                                                          (SEQ ID NO: 25)
RVKFSRSADA PAYQQGQNQL YNELNLGRRE EYDVLDKRRG RDPEMGGKPQ RRKNPQEGLY     60

NELQKDKMAE AYSEIGMKGE RRRGKGHDGL YQGLSTATKD TYDALHMQAL PPR          113
```

The coding DNA sequence thereof is as follows:

```
                                                          (SEQ ID NO: 26)
AGAGTGAAGT TCAGCAGGAG CGCAGACGCC CCCGCGTACA AGCAGGGCCA GAACCAGCTC    60

TATAACGAGC TCAATCTAGG ACGAAGAGAG GAGTACGATG TTTTGGACAA GAGACGTGGC   120

CGGGACCCTG AGATGGGGGG AAAGCCGAGA AGGAAGAACC CTCAGGAAGG CCTGTACAAT   180

GAACTGCAGA AAGATAAGAT GGCGGAGGCC TACAGTGAGA TTGGGATGAA AGGCGAGCGC   240

CGGAGGGGCA AGGGGCACGA TGGCCTTTAC CAGGGTCTCA GTACAGCCAC CAAGGACACC   300

TACGACGCCC TTCACATGCA GGCCCTGCCC CCTCGC                             336
```

Vector

The invention also provides a DNA construct encoding the CAR sequences of the invention.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically.

The present invention also provides vectors in which the DNA construct of the present invention is inserted. Vectors derived from retroviruses such as the lentivirus are suitable tools to achieve long-term gene transfer since they allow long-term, stable integration of a transgene and its propagation in daughter cells. Lentiviral vectors have the advantage over vectors derived from onco-retroviruses such as murine leukemia viruses in that they can transduce non-proliferating cells, such as hepatocytes. They also have the advantage of low immunogenicity.

In brief summary, the expression of natural or synthetic nucleic acids encoding CARs is typically achieved by operably linking a nucleic acid encoding the CAR polypeptide or portions thereof to a promoter, and incorporating the construct into an expression vector. The vectors can be suitable for replication and integration in eukaryotes. Typical cloning vectors contain transcription and translation terminators, initiation sequences, and promoters useful for regulation of the expression of the desired nucleic acid sequence.

The expression constructs of the present invention may also be used for nucleic acid immune and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector, The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors, Further, the expression vector may be provided to a cell in the form of a viral vector. Viral vector technology is well known in the art and is described, for example, in Sambrook et al, (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1a (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters, inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionein promoter, a glucocorticoid promoter, a progesterone promoter, and a tetracycline promoter.

In order to assess the expression of a CAR polypeptide or portions thereof, the expression vector to be introduced into a ceil can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

In the case where a non-viral delivery system is utilized, genome editing technique is exemplarily employed to complete the invention, for example CRISPR-Cas9, ZFN or TALEN.

In a preferred embodiment of the invention, the vector is a lentiviral vector.

In a preferred embodiment of the invention, the DNA construct further comprises a signal peptide coding sequence. Preferably, the signal peptide sequence is ligated upstream of the nucleic acid sequence of antigen binding domain. Preferably the signal peptide is a human CD8a signal peptide.

Preferably, the amino acid sequence of the signal peptide is as follows:

The amino acid sequence of CD8 leader sequence is:

```
                                        (SEQ ID NO: 27)
    MALPVTALLL PLALLLHAAR P                 21
```

The DNA sequence encoding CD8 leader sequence is:

```
                                        (SEQ ID NO: 28)
ATGGCCTTAC CAGTGACCGC CTTGCTCCTG CCGCTGGCCT TGCTGCTCCA CGCCGCCAGG   60

CCG                                                                63
```

Therapeutic Application

The present invention encompasses a cell (e.g., T cell) transduced with a lentiviral vector (LV) encoding the CAR of the invention. The transduced T cell can elicit a CAR-mediated T-cell response.

Thus, the present invention also provides a method for stimulating a T cell-mediated immune response to a target cell population or tissue in a mammal comprising the step of administering to the mammal a T cell that expresses the CAR of the invention.

In one embodiment, the present invention includes a type of cellular therapy where T cells are genetically modified to express the CAR of the invention and the CAR-T cell is infused to a recipient in need thereof. The infused cell is able to kill tumor cells in the recipient. Unlike antibody therapies, CAR-T cells are able to replicate in vivo resulting in long-term persistence that can lead to sustained tumor control.

In one embodiment, the CAR-T cells of the invention can undergo robust in vivo T cell expansion and can persist for an extended amount of time. In addition, the CAR mediated immune response may be part of an adoptive immunotherapy approach in which CAR-modified T cells induce an immune response specific to the antigen binding moiety in the CAR. For example, an anti-CD20 CAR-T cell elicits an immune response specific against cells expressing CD20.

Although the data disclosed herein specifically disclose lentiviral vector comprising anti-CD20 scFv, hinge and transmembrane domain, and 4-1BB and CD3ζ signaling domains, the invention should be construed to include any number of variations for each of the components of the construct as described elsewhere herein.

Adaptation diseases that may be treated include CD20 positive tumors and diseases caused by excessive B cells (such as autoimmune diseases, for example, lupus erythematosus, etc.). CD20 positive tumors may include CD20 positive non-solid tumors (such as hematological tumors, for example, leukemias and lymphomas) or solid tumors. Types of tumors or cancers to be treated with the CARs of the invention include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia and myeloblasts, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, mesothelioma, malignant lymphoma, pancreatic cancer and ovarian cancer.

The CAR-modified T cells of the invention may also serve as a type of vaccine for ex vivo immunization and/or in vivo therapy in a mammal. Preferably, the mammal is a human.

With respect to ex vivo immunization, at least one of the following occurs in vitro prior to administering the cell into a mammal: i) expansion of the cells, ii) introducing a nucleic acid encoding a CAR to the cells, and/or iii) cryopreservation of the cells.

Ex vivo procedures are well known in the art and are discussed more fully below. Briefly, cells are isolated from a mammal (preferably a human) and genetically modified (i.e., transduced or transfected in vitro) with a vector expressing a CAR disclosed herein. The CAR-modified cell can be administered to a mammalian recipient to provide a therapeutic benefit. The mammalian recipient may be a human and the CAR-modified cell can be autologous with respect to the recipient. Alternatively, the cells can be allogeneic, syngeneic or xenogeneic with respect to the recipient.

In addition to using a cell-based vaccine in terms of ex vivo immunization, the present invention also provides compositions and methods for in vivo immunization to elicit an immune response directed against an antigen in a patient.

Generally, the cells activated and expanded as described herein may be utilized in the treatment and prevention of diseases that arise in individuals who are immunocompromised. In particular, the CAR-modified T cells of the invention are used in the treatment of CCL. In certain embodiments, the cells of the invention are used in the treatment of patients at risk for developing CCL. Thus, the present invention provides methods for the treatment or prevention of CCL comprising administering to a subject in need thereof, a therapeutically effective amount of the CAR-modified T cells of the invention.

The CAR-modified T cells of the present invention may be administered either alone, or as a pharmaceutical composition in combination with diluents and/or with other components such as IL-2, IL-17 or other cytokines or cell populations. Briefly, pharmaceutical compositions of the present invention may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount", "an anti-tumor effective amount", "an tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, preferably $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319: 1676, 1988). The optimal dosage and treatment regime for a particular patient can readily be determined by one skilled in the art of medicine by monitoring the patient for signs of disease and adjusting the treatment accordingly.

The administration of the subject compositions may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In one embodiment, the T cell compositions of the present invention are administered to a patient by intradermal or subcutaneous injection. In another embodiment, the T cell compositions of the present invention are preferably administered by i.v. injection. The compositions of T cells may be injected directly into a tumor, lymph node, or site of infection.

In certain embodiments of the present invention, cells activated and expanded using the methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunotherapeutic agents. In a further embodiment, the cell compositions of the present invention are administered to a patient in conjunction with (e.g., before, simultaneously or following) bone marrow transplantation, or the use of chemotherapy agents such as, fludarabine, external-beam radiation therapy (XRT), cyclophosphamide. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The dosage of the above treatments to be administered to a patient will vary with the precise nature of the condition being treated and the recipient of the treatment. The scaling of dosages for human administration can be performed according to art-accepted practices. In general, $1\times10^6$ to $1\times10^{10}$ of the modified T cells of the invention (e.g., CAR-T 20 cells) can be applied to patients by means of, for example, intravenous infusion each treatment or each course of treatment.

The advantages of the present invention include:

(1) As for the chimeric antigen receptor of the present invention, the extracellular antigen binding domain thereof is a specific anti-CD20 scFv. The CAR formed by binding the specific anti-CD20 scFv to a specific hinge region and an intracellular domain shows a great capability of killing tumor cells with low cytotoxicity and low side effects.

(2) The chimeric antigen receptor provided by the invention can achieve stable expression and membrane localization of CAR protein after T cells is infected by lentivirus carrying CAR gene.

(3) The CAR-modified T cell of the present invention has a longer survival time in vivo and strong anti-tumor efficacy. The optimized CAR with the IgG4 Hinge-CH2-CH3 linker region can avoid the binding of the Fc receptor and the subsequent ADCC effect (antibody-dependent cytotoxicity).

Example 1 Construction of Lentiviral Expression Vector

The full-length DNA synthesis and cloning construction of coding plasmids were commissioned by Shanghai Boyi Biotechnology Co., Ltd. Different anti-CD20 scFv coding sequences were used in each plasmid. The cloning vector was selected as pWPT lentiviral vector. The cloning sites were BamH I and Sal I sites. The specific sequence structure is shown in FIG. 1. The amino acid and nucleotide sequences of each element are as described above.

In the following examples, CAR-T20.13, CAR-T20.14, CAR-T20.16, CAR-T20.19, CAR-T20.20 with better effects are taken as examples.

Example 2 Preparation of CAR-T Cell (1) After taking venous blood from healthy people, mononuclear cells (PBMCs) were isolated by density gradient centrifugation.

(2) On day 0, PBMCs were cultured in GT-T551 cell culture medium containing 2% human albumin, and the final concentration of cells was adjusted to $2 \times 10^6$ cells/mL. The cells were seeded in a cell culture flask previously coated with Retronectin (purchased from TAKARA) at a final concentration of 10 μg/mL and CD3 monoclonal antibody (OKT3) at a final concentration of 5 μg/mL. Recombinant human interleukin 2 (IL-2) was added to the culture medium at a final concentration of 1000 U/mL. The cells were cultured in an incubator with a saturated humidity and 5% $CO_2$ at 37° C.

(3) On day 2, fresh medium, concentrated and purified CAR20 lentivirus solution, protamine sulfate (12 μg/ml), and IL-2 (at a final concentration of 1000 U/mL) were added. After 12 hours of infection in a 5% $CO_2$ incubator at 37° C., the culture medium was discarded, fresh medium was added, and cultivation was continued in a 5% $CO_2$ incubator at 37° C.

(4) Starting from day 6, CART20 cells can be taken for the corresponding activity assay.

In the present invention, the preparation process of CAR-modified T cell targeting CD20 antigen is improved, and GT-551 serum-free medium supplemented with 2% human albumin was selected to culture lymphocytes in vitro.

Figure 2:
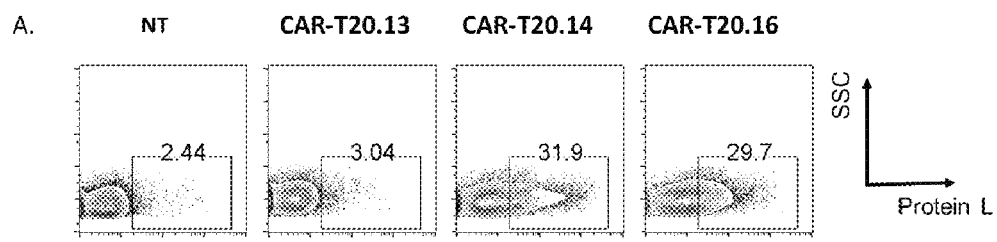
FIG. 2 shows detection of transfection efficiency of engineered T cell with chimeric antigen receptors targeting CD20. The expression level of the CAR gene-encoded protein on the surface of the T cell membrane in CAR-T20s cells cultured on day 7 (A) and day 11 (B) was identified by the Protein L method.
Figure 2:
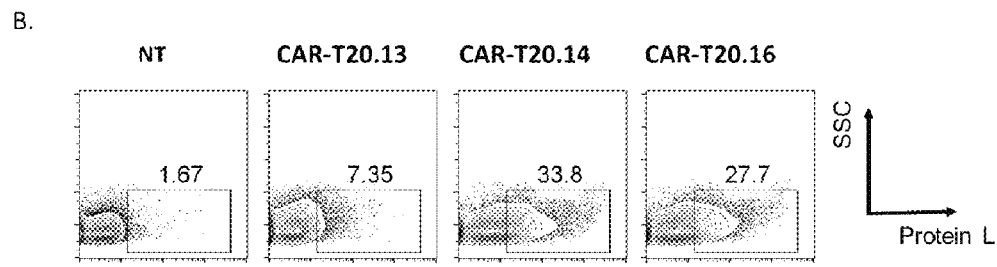

Example 3 Detection of the Integration Rate of the CAR Gene in the T Cell Genome and the Expression Level of the Encoded Protein Thereof on the Membrane Surface $0.5 \times 10^6$ of CART-20 cell samples cultured on day 7 (FIG. 2A and FIG. 5A) and day 11 (FIG. 2B) in Example 2 were taken, respectively. The expression level of CAR20 protein on the surface of T cell membrane was analyzed by flow cytometry after Protein L staining. The results showed that, except for CAR-T20.13, all of the CAR structures designed in this study can detect the chimeric antigen receptor localization on the cell membrane surface of the corresponding modified T cells using Protein L.

Example 4 Detection of the In Vitro Activation Ability of CAR-T20s

The deCAR-T20 cells cultured on day 6 in Example 2 were co-cultured with target cells. Then the up-regulated level of CD137 and the secretion level of IFNγ in the culture supernatant were examined. $1 \times 10^5$ of CART-20 cells (cultured on day 6) were cultured respectively with CD20-positive RAJI and RAMOS tumor cell lines, and CD20-negative MOLT-4 tumor cell line, or without tumor cells, in 200 μl GT-551 medium for 18 h in a ratio of 1:1. Then the expression level of CD137 on the surface of T cell membrane was detected by flow cytometry (FIG. 3A) and the secretion level of IFNγ in the culture supernatant was detected by ELISA (FIG. 3B).

Figure 3:
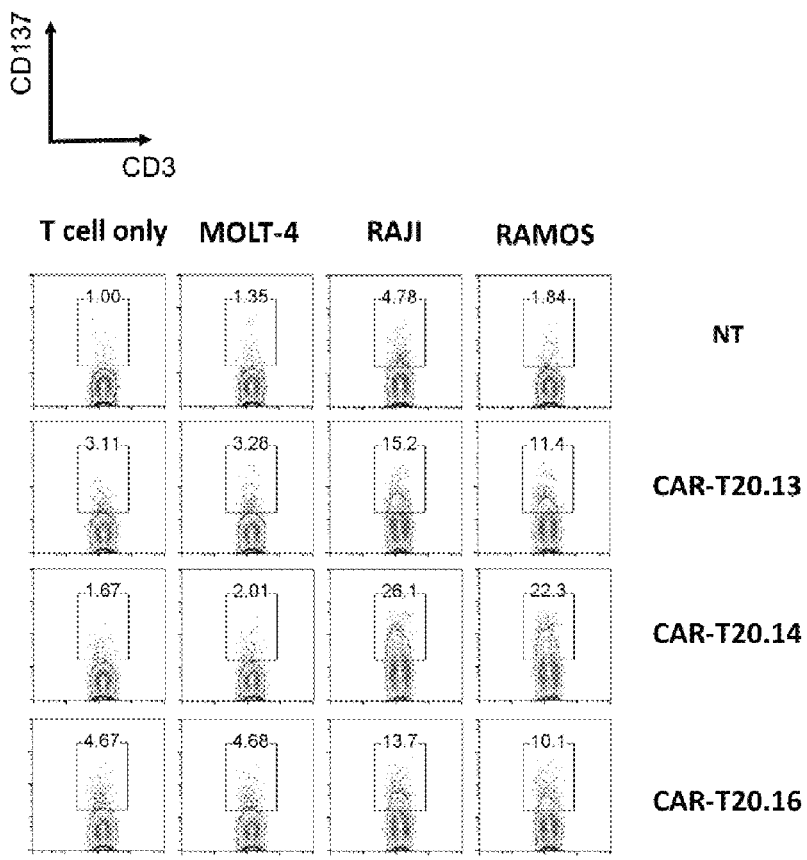
FIG. 3. $1*10^5$ of NT, CART-20.13, CART-20.14 and CAR-T20.16 cells (cultured on day 6) were co-cultured respectively with CD20-positive RAJI and RAMOS tumor cell lines, and CD20-negative MOLT-4 tumor cell line in 200 μl GT-551 medium for 18 h in a ratio of 1:1. Then the expression level of CD137 on the surface of T cell membrane (A) and the secretion level of IFNγ in the co-culture supernatant (B) were detected.
Figure 3:
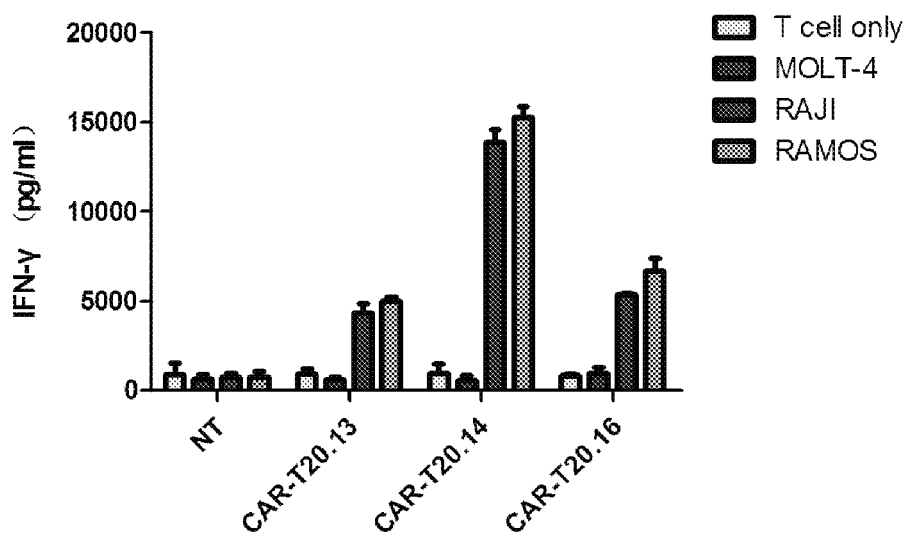

From the results in FIG. 3, we could concluded that the CAR based on Obinutuzumab also achieved expression and membrane surface localization in the corresponding modified cells, but the CAR structure based on the Ofatumumab sequence showed better in vitro activation ability and specificity targeting antigen when compared with the CAR constructed based on Obinutuzumab and Rituximab.

Example 5 Detection of the CAR-T20s Cells Induced Early Apoptosis Activity of Tumor Cells CART-20.13, CART-20.14 and CAR-T20.16 cells (cultured on day 11) from Example 2 were co-cultured respectively with $1 \times 10^4$ of CFSE-labeled CD20-negative (MOLT-4) or CD20-positive (RAJI, RAMOS) tumor cell lines in 200 μl GT-551 medium for 4 h. Then the cell pellet was collected by centrifugation. The cells were washed twice with PBS and stained for 30 min with Annexin V-APC dye in a ratio of 1:50 in 100 μl of dyeing solution. After washing with PBSonce, the proportion of Annexin V positive cells in CFSE positive cells was analyzed on a flow cytometry.

Figure 4:
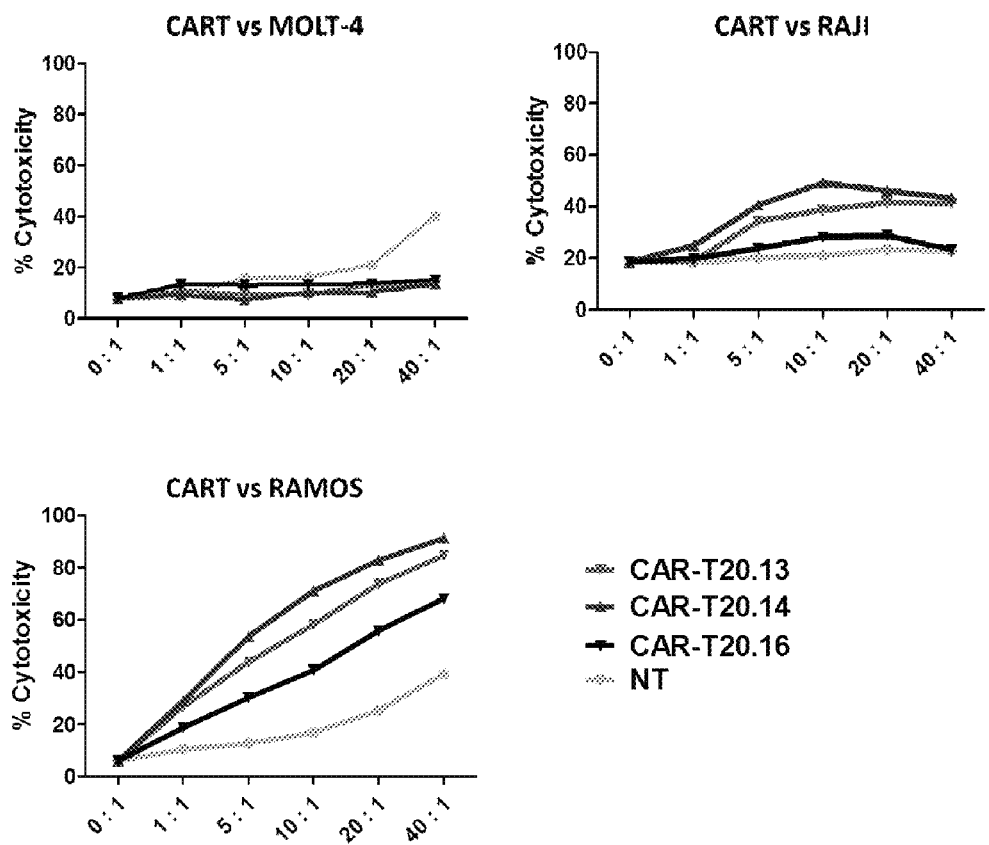
FIG. 4 shows detection of apoptosis levels of tumor cells induced by CART-20. $1*10^4$ of CFSE-labeled CD20-negative (MOLT-4) or CD20-positive (RAJI, RAMOS) tumor cell lines were co-cultured respectively with NT, CART-20.13, CART-20.14 and CAR-T20.16 cells (cultured on day 11) in 200 μl GT-551 medium for 4 h according to the ratio as shown in figure. Then the cell pellet was collected by centrifugation. The cells were washed twice with PBS and stained for 30 min with Annexin V-APC dye in a ratio of 1:50 in 100 μl of dyeing solution. After washing with PBS for 1 time, the proportion of Annexin V positive cells in CFSE positive cells was analyzed on a flow cytometry. The results in figure show the statistical analysis of Annexin V positive cells in the corresponding co-culture samples.

The results in FIG. 4 show that the CAR structure based on the Ofatumumab sequence shows better ability to induce early apoptosis of CD20 target cells in vitro when compared with the CAR constructed based on Obinutuzumab and Rituximab.

Example 6 Identification of the In Vitro Activation Ability of the Third Generation Chimeric Antigen Receptor and the Chimeric Antigen Receptor with Mutation in Hinge Region (1) Under the condition that the transfection rate was basically equal (FIG. 5A), the CAR-T20s cells (prepared by the method of Example 2) cultured on the day 7 were cultured respectively with K562, K562 stable transfected cells of CD19 single positive, CD20 single positive, CD19 and CD20 double positive, and RAJI target cell (each taking $1 \times 10^5$ cells) in 200 μl GT-551 medium for 18 h in a ratio of 1:1. Then the up-regulated level of CD137 (FIG. 5B) and the secretion level of IFNγ in the culture supernatant (FIG. 5C) were detected.

Figure 5:
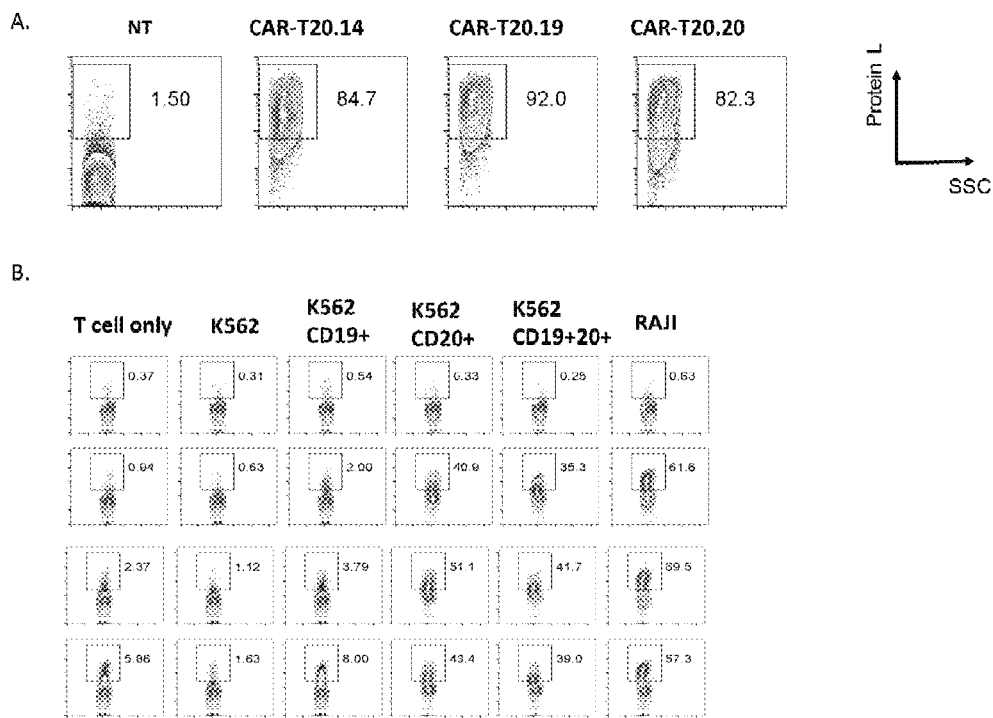
FIG. 5 shows identification of the activation ability in vitro of the third generation chimeric antigen receptor and the chimeric antigen receptor with mutation in hinge region (which are constructed based on the sequence of Ofatumumaband antibody). The expression level of the CAR gene-encoded protein (A) on the surface of the T cell membrane in CAR-T20.14, CAR-T20.19 and CAR-T20.20 cells cultured on day 7 was identified by the Protein L method. $1*10^5$ of NT, CART-20.14, CART-20.19 and CAR-T20.20 cells (cultured on day 7) were cultured respectively with K562, K562 stable transfected cells of CD19 single positive, CD20 single positive, CD19 and CD20 double positive, and RAJI target cell in 200 μl GT-551 medium for 18 h in a ratio of 1:1. Then the expression level of CD137 on the surface of T cell membrane (B) and the secretion level of IFNγ in the culture supernatant (C) were detected, respectively.
Figure 5:
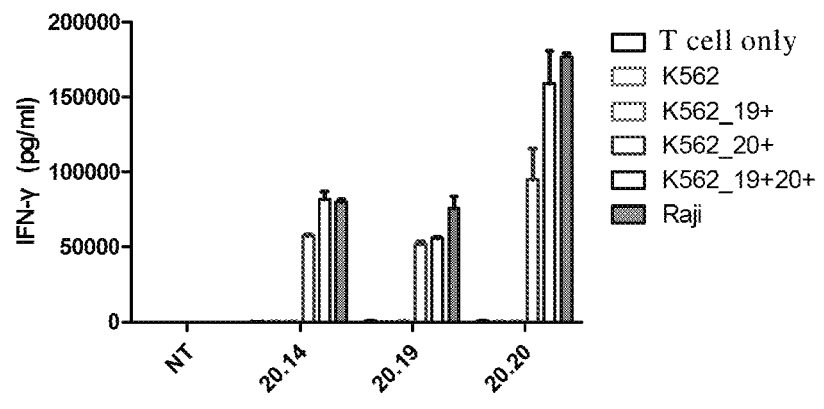

(2) The results shown in FIG. 5 indicate that the in vitro activation ability (CD137 and IFNg) of the chimeric antigen receptor CAR-T20.14 and CAR-T20.19 (having a mutation in the hinge region) is substantially equivalent, in the case of substantially identical infection efficiency. The third generation CAR structure CAR-T20.20 shows better in vitro activation capacity (CD137 and IFNγ) than the second generation CAR-T20.14 and CAR-T20.19.

Example 7. Detection of the Ability of CAR-T20 Cells to Scavenge CD20 Positive Cells In Vivo (1) Raji-Luc cells expressing luciferase were injected into NCG mice ($5 \times 10^5$/mouse) through the tail vein. One week after the inoculation, the in vivo expansion of the tumor cells was observed by in vivo imaging and recorded as Day 0. NT and CAR-T20.19 cells were injected into Day 0 mice ($5 \times 10^6$/mouse) through the tail vein. On Day0, Day7, Day14, Day21, the expansion of tumor cells in mice was observed by in vivo imaging and analyzed based on changes in fluorescence intensity and body weight changes of mice.

Figure 6:
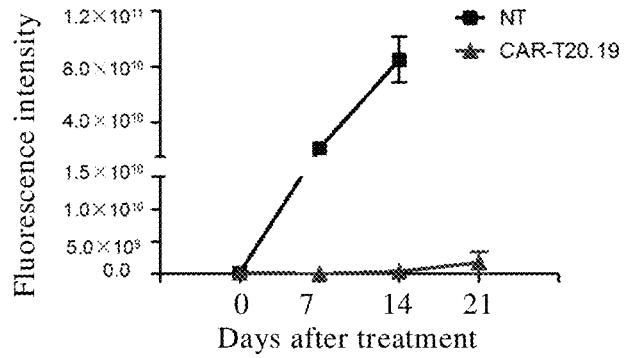
FIG. 6 shows the detection results of the ability of CAR-T20 cells to scavenge CD20-positive cells in vivo. The results indicate that CAR-T20.19 can effectively inhibit the in vivo expansion of CD20-positive tumor cells.

(2) The results shown in FIG. 6 indicate that CAR-T20.19 can effectively inhibit the in vivo expansion of CD20-positive tumor cells.

The preferred embodiments of the present invention are described in detail above, but the present invention is not limited to the specific details in above embodiments. Various simple modifications can be made to the technical solutions of the present invention within the scope of the technical idea of the present invention. These simple variants all fall within the protection scope of the present invention.

It should be further noted that the specific technical features described in the above specific embodiments may be combined in any suitable manner without contradiction. To avoid unnecessary repetition, the various possible combinations of the invention are not described separately.

In addition, any combination of various embodiments of the invention may be made as long as it does not deviate from the idea of the invention, and it should be regarded as the disclosure of the invention.

The invention claimed is:

1. A method of treating a B-cell malignancy, the method comprising administering a T cell expressing a chimeric antigen receptor (CAR) to a subject in need thereof, wherein the CAR comprises an anti-CD20 antigen binding region comprising:
   (i) a heavy chain variable region ($V_H$) having an amino acid sequence set forth in SEQ ID NO: 7, and
   (ii) a light chain variable region ($V_L$) having an amino acid sequence set forth in SEQ ID NO: 11,
   wherein $V_H$ is located at the N-terminus of $V_L$,
   wherein the CAR comprises an amino acid sequence set forth in SEQ ID NO: 5.

2. The method of claim 1, wherein the B-cell malignancy is Hodgkin's lymphoma, non-Hodgkin's lymphoma, leukemia, and/or multiple myeloma.

3. The method of claim 1, wherein the B-cell malignancy is acute lymphocytic leukemia (ALL), chronic lymphocytic leukemia (CLL), e B-cell acute lymphoblastic leukemia (B-ALL), B-cell leukemia, or B cell lymphoma.

4. The method of claim 1, wherein the immune T cell is administered by infusion, injection, transfusion, implantation, and/or transplantation.

5. The method of claim 1, wherein the T cell is administered intravenously, subcutaneously, intranodally, intramedullary, intramuscularly, or intraperitoneally.

6. The method of claim 1, wherein the T cell is administered via intravenous infusion.

7. The method of claim 1, wherein the T cell is allogeneic or autologous.

8. The method of claim 1, wherein the subject is a human.

* * * * *

SEQUENCE LISTING

```
<160> NUMBER OF SEQ ID NOS: 40

<210> SEQ ID NO 1
<211> LENGTH: 672
<212> TYPE: PRT
<213> ORGANISM: Artificial Sequence
<220> FEATURE:
<223> OTHER INFORMATION: CAR

<400> SEQUENCE: 1

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Pro Gly Arg Ser Leu Arg Leu Ser Cys Ala Ala Ser Gly Phe
        35                  40                  45

Thr Phe Asn Asp Tyr Ala Met His Trp Val Arg Gln Ala Pro Gly Lys
    50                  55                  60

Gly Leu Glu Trp Val Ser Thr Ile Ser Trp Asn Ser Gly Ser Ile Gly
65                  70                  75                  80

Tyr Ala Asp Ser Val Lys Gly Arg Phe Thr Ile Ser Arg Asp Asn Ala
                85                  90                  95

Lys Lys Ser Leu Tyr Leu Gln Met Asn Ser Leu Arg Ala Glu Asp Thr
            100                 105                 110

Ala Leu Tyr Tyr Cys Ala Lys Asp Ile Gln Tyr Gly Asn Tyr Tyr Tyr
        115                 120                 125

Gly Met Asp Val Trp Gly Gln Gly Thr Thr Val Thr Val Ser Ser Gly
    130                 135                 140

Gly Gly Gly Ser Gly Gly Gly Gly Ser Gly Gly Gly Gly Ser Glu Ile
145                 150                 155                 160

Val Leu Thr Gln Ser Pro Ala Thr Leu Ser Leu Ser Pro Gly Glu Arg
                165                 170                 175

Ala Thr Leu Ser Cys Arg Ala Ser Gln Ser Val Ser Ser Tyr Leu Ala
            180                 185                 190

Trp Tyr Gln Gln Lys Pro Gly Gln Ala Pro Arg Leu Leu Ile Tyr Asp
        195                 200                 205

Ala Ser Asn Arg Ala Thr Gly Ile Pro Ala Arg Phe Ser Gly Ser Gly
    210                 215                 220

Ser Gly Thr Asp Phe Thr Leu Thr Ile Ser Ser Leu Glu Pro Glu Asp
225                 230                 235                 240

Phe Ala Val Tyr Tyr Cys Gln Gln Arg Ser Asn Trp Pro Ile Thr Phe
                245                 250                 255

Gly Gln Gly Thr Arg Leu Glu Ile Lys Glu Ser Lys Tyr Gly Pro Pro
            260                 265                 270

Cys Pro Pro Cys Pro Ala Pro Glu Phe Leu Gly Gly Pro Ser Val Phe
        275                 280                 285
```

-continued

Leu Phe Pro Pro Lys Pro Lys Asp Thr Leu Met Ile Ser Arg Thr Pro
    290                 295                 300

Glu Val Thr Cys Val Val Val Asp Val Ser Gln Glu Asp Pro Glu Val
305                 310                 315                 320

Gln Phe Asn Trp Tyr Val Asp Gly Val Glu Val His Asn Ala Lys Thr
                325                 330                 335

Lys Pro Arg Glu Glu Gln Phe Asn Ser Thr Tyr Arg Val Val Ser Val
            340                 345                 350

Leu Thr Val Leu His Gln Asp Trp Leu Asn Gly Lys Glu Tyr Lys Cys
        355                 360                 365

Lys Val Ser Asn Lys Gly Leu Pro Ser Ser Ile Glu Lys Thr Ile Ser
370                 375                 380

Lys Ala Lys Gly Gln Pro Arg Glu Pro Gln Val Tyr Thr Leu Pro Pro
385                 390                 395                 400

Ser Gln Glu Glu Met Thr Lys Asn Gln Val Ser Leu Thr Cys Leu Val
                405                 410                 415

Lys Gly Phe Tyr Pro Ser Asp Ile Ala Val Glu Trp Glu Ser Asn Gly
            420                 425                 430

Gln Pro Glu Asn Asn Tyr Lys Thr Thr Pro Pro Val Leu Asp Ser Asp
        435                 440                 445

Gly Ser Phe Phe Leu Tyr Ser Arg Leu Thr Val Asp Lys Ser Arg Trp
450                 455                 460

Gln Glu Gly Asn Val Phe Ser Cys Ser Val Met His Glu Ala Leu His
465                 470                 475                 480

Asn His Tyr Thr Gln Lys Ser Leu Ser Leu Ser Leu Gly Lys Ile Tyr
                485                 490                 495

Ile Trp Ala Pro Leu Ala Gly Thr Cys Gly Val Leu Leu Leu Ser Leu
            500                 505                 510

Val Ile Thr Leu Tyr Cys Lys Arg Gly Arg Lys Lys Leu Leu Tyr Ile
        515                 520                 525

Phe Lys Gln Pro Phe Met Arg Pro Val Gln Thr Thr Gln Glu Glu Asp
530                 535                 540

Gly Cys Ser Cys Arg Phe Pro Glu Glu Glu Gly Gly Cys Glu Leu
545                 550                 555                 560

Arg Val Lys Phe Ser Arg Ser Ala Asp Ala Pro Ala Tyr Lys Gln Gly
                565                 570                 575

Gln Asn Gln Leu Tyr Asn Glu Leu Asn Leu Gly Arg Arg Glu Glu Tyr
            580                 585                 590

Asp Val Leu Asp Lys Arg Arg Gly Arg Asp Pro Glu Met Gly Gly Lys
        595                 600                 605

Pro Arg Arg Lys Asn Pro Gln Glu Gly Leu Tyr Asn Glu Leu Gln Lys
610                 615                 620

Asp Lys Met Ala Glu Ala Tyr Ser Glu Ile Gly Met Lys Gly Glu Arg
625                 630                 635                 640

Arg Arg Gly Lys Gly His Asp Gly Leu Tyr Gln Gly Leu Ser Thr Ala
                645                 650                 655

Thr Lys Asp Thr Tyr Asp Ala Leu His Met Gln Ala Leu Pro Pro Arg
            660                 665                 670

<210> SEQ ID NO 2
<211> LENGTH: 2019
<212> TYPE: DNA
<213> ORGANISM: Artificial Sequence
<220> FEATURE:
<223> OTHER INFORMATION: CAR

<400> SEQUENCE: 2

```
atggccttac cagtgaccgc cttgctcctg ccgctggcct tgctgctcca cgccgccagg      60
ccggaagtgc agctggtgga gtctggggga ggcttggtac agcctggcag gtccctgaga     120
ctctcctgtg cagcctctgg attcaccttt aatgattatg ccatgcactg ggtccggcaa     180
gctccaggga agggcctgga gtgggtctca actattagtt ggaatagtgg ttccataggc     240
tatgcggact ctgtgaaggg ccgattcacc atctccagag acaacgccaa gaagtccctg     300
tatctgcaaa tgaacagtct gagagctgag gacacggcct tgtattactg tgcaaaagat     360
atacagtacg gcaactacta ctacggtatg gacgtctggg gccaagggac cacggtcacc     420
gtctcctcag gtggcggtgg ctcgggcggt ggtgggtcgg gtggcggcgg atctgaaatt     480
gtgttgacac agtctccagc caccctgtct ttgtctccag gggaaagagc caccctctcc     540
tgcagggcca gtcagagtgt tagcagctac ttagcctggt accaacagaa acctggccag     600
gctcccaggc tcctcatcta tgatgcatcc aacagggcca ctggcatccc agccaggttc     660
agtggcagtg ggtctgggac agacttcact ctcaccatca gcagcctaga gcctgaagat     720
tttgcagttt attactgtca gcagcgtagc aactggccga tcaccttcgg ccaagggaca     780
cgactggaga ttaaagagag caagtacgga ccgccctgcc ccccttgccc tgccccgag     840 ttcctgggcg gacccagcgt gttcctgttc ccccccaagc ccaaggacac cctgatgatc     900
agccggaccc ccgaggtgac ctgcgtggtg gtggacgtga gccaggaaga tcccgaggtc     960
cagttcaatt ggtacgtgga cggcgtggaa gtgcacaacg ccaagaccaa gcccagagag    1020
gaacagttca acagcaccta ccgggtggtg tctgtgctga ccgtgctgca ccaggactgg    1080
ctgaacggca agaatacaa gtgcaaggtg tccaacaagg gcctgcccag cagcatcgaa    1140
aagaccatca gcaaggccaa gggccagcct cgcgagcccc aggtgtacac cctgcctccc    1200
tcccaggaag agatgaccaa gaaccaggtg tccctgacct gcctggtgaa gggcttctac    1260
cccagcgaca tcgccgtgga gtgggagagc aacggccagc ctgagaacaa ctacaagacc    1320
accccctccg tgctggacag cgacggcagc ttcttcctgt acagccggct gaccgtggac    1380
aagagccggt ggcaggaagg caacgtcttt agctgcagcg tgatgcacga ggccctgcac    1440
aaccactaca cccagaagag cctgagcctg tccctgggca gatctacat ctgggcgccc    1500 ttggccggga cttgtggggt ccttctcctg tcactggtta tcacccttta ctgcaaacgg    1560
ggcagaaaga aactcctgta tatattcaaa caaccattta tgagaccagt acaaactact    1620
caagaggaag atggctgtag ctgccgattt ccagaagaag aagaaggagg atgtgaactg    1680
agagtgaagt tcagcaggag cgcagacgcc cccgcgtaca gcagggcca gaaccagctc    1740 tataacgagc tcaatctagg acgaagagag gagtacgatg ttttggacaa gagacgtggc    1800
cgggaccctg agatggggg aaagccgaga aggaagaacc ctcaggaagg cctgtacaat    1860
gaactgcaga agataagat ggcggaggcc tacagtgaga ttgggatgaa aggcgagcgc    1920
cggaggggca aggggcacga tggcctttac cagggtctca gtacagccac caaggacacc    1980
tacgacgccc ttcacatgca ggccctgccc cctcgctag                         2019
```

<210> SEQ ID NO 3
<211> LENGTH: 670
<212> TYPE: PRT
<213> ORGANISM: Artificial Sequence
<220> FEATURE:
<223> OTHER INFORMATION: CAR

<400> SEQUENCE: 3

Met Ala Leu Pro Val Thr Ala Leu Leu Leu Pro Leu Ala Leu Leu Leu
1               5                   10                  15

His Ala Ala Arg Pro Gln Val Gln Leu Gln Gln Pro Gly Ala Glu Leu
            20                  25                  30

Val Lys Pro Gly Ala Ser Val Lys Met Ser Cys Lys Ala Ser Gly Tyr
        35                  40                  45

Thr Phe Thr Ser Tyr Asn Met His Trp Val Lys Gln Thr Pro Gly Arg
    50                  55                  60

Gly Leu Glu Trp Ile Gly Ala Ile Tyr Pro Gly Asn Gly Asp Thr Ser
65                  70                  75                  80

Tyr Asn Gln Lys Phe Lys Gly Lys Ala Thr Leu Thr Ala Asp Lys Ser
                85                  90                  95

Ser Ser Thr Ala Tyr Met Gln Leu Ser Ser Leu Thr Ser Glu Asp Ser
            100                 105                 110

Ala Val Tyr Tyr Cys Ala Arg Ser Thr Tyr Tyr Gly Gly Asp Trp Tyr
        115                 120                 125

Phe Asn Val Trp Gly Ala Gly Thr Thr Val Thr Val Ser Ala Gly Gly
    130                 135                 140

Gly Gly Ser Gly Gly Gly Gly Ser Gly Gly Gly Gly Ser Gln Ile Val
145                 150                 155                 160

Leu Ser Gln Ser Pro Ala Ile Leu Ser Ala Ser Pro Gly Glu Lys Val
                165                 170                 175

Thr Met Thr Cys Arg Ala Ser Ser Ser Val Ser Tyr Ile His Trp Phe
            180                 185                 190

Gln Gln Lys Pro Gly Ser Ser Pro Lys Pro Trp Ile Tyr Ala Thr Ser
        195                 200                 205

Asn Leu Ala Ser Gly Val Pro Val Arg Phe Ser Gly Ser Gly Ser Gly
    210                 215                 220

Thr Ser Tyr Ser Leu Thr Ile Ser Arg Val Glu Ala Glu Asp Ala Ala
225                 230                 235                 240

Thr Tyr Tyr Cys Gln Gln Trp Thr Ser Asn Pro Pro Thr Phe Gly Gly
                245                 250                 255

Gly Thr Lys Leu Glu Ile Lys Glu Ser Lys Tyr Gly Pro Pro Cys Pro
            260                 265                 270

Pro Cys Pro Ala Pro Glu Phe Leu Gly Gly Pro Ser Val Phe Leu Phe
        275                 280                 285

Pro Pro Lys Pro Lys Asp Thr Leu Met Ile Ser Arg Thr Pro Glu Val
    290                 295                 300

Thr Cys Val Val Val Asp Val Ser Gln Glu Asp Pro Glu Val Gln Phe
305                 310                 315                 320

Asn Trp Tyr Val Asp Gly Val Glu Val His Asn Ala Lys Thr Lys Pro
                325                 330                 335

Arg Glu Glu Gln Phe Asn Ser Thr Tyr Arg Val Val Ser Val Leu Thr
            340                 345                 350

Val Leu His Gln Asp Trp Leu Asn Gly Lys Glu Tyr Lys Cys Lys Val
        355                 360                 365

Ser Asn Lys Gly Leu Pro Ser Ser Ile Glu Lys Thr Ile Ser Lys Ala
    370                 375                 380

Lys Gly Gln Pro Arg Glu Pro Gln Val Tyr Thr Leu Pro Pro Ser Gln
385                 390                 395                 400

Glu Glu Met Thr Lys Asn Gln Val Ser Leu Thr Cys Leu Val Lys Gly
                405                 410                 415

```
Phe Tyr Pro Ser Asp Ile Ala Val Glu Trp Glu Ser Asn Gly Gln Pro
            420                 425                 430

Glu Asn Asn Tyr Lys Thr Thr Pro Val Leu Asp Ser Asp Gly Ser
            435                 440                 445

Phe Phe Leu Tyr Ser Arg Leu Thr Val Asp Lys Ser Arg Trp Gln Glu
    450                 455                 460

Gly Asn Val Phe Ser Cys Ser Val Met His Glu Ala Leu His Asn His
465                 470                 475                 480

Tyr Thr Gln Lys Ser Leu Ser Leu Ser Leu Gly Lys Ile Tyr Ile Trp
                485                 490                 495

Ala Pro Leu Ala Gly Thr Cys Gly Val Leu Leu Leu Ser Leu Val Ile
            500                 505                 510

Thr Leu Tyr Cys Lys Arg Gly Arg Lys Lys Leu Leu Tyr Ile Phe Lys
            515                 520                 525

Gln Pro Phe Met Arg Pro Val Gln Thr Thr Gln Glu Glu Asp Gly Cys
            530                 535                 540

Ser Cys Arg Phe Pro Glu Glu Glu Gly Gly Cys Glu Leu Arg Val
545                 550                 555                 560

Lys Phe Ser Arg Ser Ala Asp Ala Pro Ala Tyr Lys Gln Gly Gln Asn
                565                 570                 575

Gln Leu Tyr Asn Glu Leu Asn Leu Gly Arg Arg Glu Glu Tyr Asp Val
            580                 585                 590

Leu Asp Lys Arg Arg Gly Arg Asp Pro Glu Met Gly Gly Lys Pro Arg
            595                 600                 605

Arg Lys Asn Pro Gln Glu Gly Leu Tyr Asn Glu Leu Gln Lys Asp Lys
        610                 615                 620

Met Ala Glu Ala Tyr Ser Glu Ile Gly Met Lys Gly Glu Arg Arg Arg
625                 630                 635                 640

Gly Lys Gly His Asp Gly Leu Tyr Gln Gly Leu Ser Thr Ala Thr Lys
                645                 650                 655

Asp Thr Tyr Asp Ala Leu His Met Gln Ala Leu Pro Pro Arg
            660                 665                 670

<210> SEQ ID NO 4
<211> LENGTH: 2013
<212> TYPE: DNA
<213> ORGANISM: Artificial Sequence
<220> FEATURE:
<223> OTHER INFORMATION: CAR

<400> SEQUENCE: 4
atggcctcac cagtgaccgc cttgctcctg ccgctggcct tgctgctcca cgccgccagg     60
ccgcaggtgc agttgcaaca gcctggagct gagttggtga agcctggtgc ttctgtgaag    120
atgtcttgta aggcttctgg atacacattc acttcttaca catgcactg  ggtgaagcag    180 actcctggta ggggtttgga gtggatcgga gctatctacc caggaaacgg agacacatct    240
tacaaccaga gttcaagggt aaggctaca ttgactgctg acaagtcttc atctactgct    300
tacatgcaat tgtcttcttt gacatctgag gactctgcag tttactactg cgctaggtct    360
acatactacg gaggtgactg gtacttcaac gtgtggggag caggtaccac ggtcactgtc    420
tctgcaggtg gaggtggatc tggaggagga ggatctggtg gaggaggttc tcaaattgtt    480
ctctcccagt ctccagcaat cctgtcagct ctcctggaga gaaggtgac tatgacttgc    540 agggcttctt catctgtttc ttacatccac tggttccagc agaagcctgg ttcttcacct    600
```

```
aagccttgga tctacgctac atctaacttg gcatctggag tgcctgtgag gttctctggt    660
tctggttcag gtacttctta ctctttgaca atctctaggg tggaggctga ggacgctgct    720
acttactact gccagcagtg gacatctaac cctccaacat tcggaggtgg tactaagttg    780
gagatcaagg agagcaagta cggaccgccc tgccccctt gccctgcccc cgagttcctg     840
ggcggaccca gcgtgttcct gttcccccc aagcccaagg acaccctgat gatcagccgg     900
acccccgagg tgacctgcgt ggtggtggac gtgagccagg aagatcccga ggtccagttc    960
aattggtacg tggacggcgt ggaagtgcac aacgccaaga ccaagcccag agaggaacag   1020
ttcaacagca cctaccgggt ggtgtctgtg ctgaccgtgc tgcaccagga ctggctgaac   1080
ggcaaagaat acaagtgcaa ggtgtccaac aagggcctgc ccagcagcat cgaaaagacc   1140
atcagcaagg ccaagggcca gcctcgcgag ccccaggtgt acaccctgcc tccctcccag   1200
gaagagatga ccaagaacca ggtgtccctg acctgcctgg tgaagggctt ctaccccagc   1260
gacatcgccg tggagtggga gagcaacggc cagcctgaga caactacaa gaccacccct    1320
cccgtgctgg acagcgacgg cagcttcttc ctgtacagcc ggctgaccgt ggacaagagc   1380
cggtggcagg aaggcaacgt ctttagctgc agcgtgatgc acgaggccct gcacaaccac   1440
tacacccaga gagcctgag cctgtccctg ggcaagatct acatctgggc gcccttggcc    1500
gggacttgtg gggtccttct cctgtcactg gttatcaccc tttactgcaa acggggcaga   1560
aagaaactcc tgtatatatt caaacaacca tttatgagac cagtacaaac tactcaagag   1620
gaagatggct gtagctgccg atttccagaa gaagaagaag gaggatgtga actgagagtg   1680
aagttcagca ggagcgcaga cgcccccgcg tacaagcagg ccagaaccca gctctataac   1740
gagctcaatc taggacgaag agaggagtac gatgttttgg acaagagacg tggccgggac   1800
cctgagatgg ggggaaagcc gagaaggaag aaccctcagg aaggcctgta caatgaactg   1860
cagaaagata agatggcgga ggcctacagt gagattggga tgaaggcga gcgccggagg    1920
ggcaaggggc acgatggcct ttaccagggt ctcagtacag ccaccaagga cacctacgac   1980
gcccttcaca tgcaggccct gccccctcgc tag                                 2013
```

<210> SEQ ID NO 5
<211> LENGTH: 672
<212> TYPE: PRT
<213> ORGANISM: Artificial Sequence
<220> FEATURE:
<223> OTHER INFORMATION: CAR

<400> SEQUENCE: 5

```
Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Pro Gly Arg Ser Leu Arg Leu Ser Cys Ala Ala Ser Gly Phe
        35                  40                  45

Thr Phe Asn Asp Tyr Ala Met His Trp Val Arg Gln Ala Pro Gly Lys
    50                  55                  60

Gly Leu Glu Trp Val Ser Thr Ile Ser Trp Asn Ser Gly Ser Ile Gly
65                  70                  75                  80

Tyr Ala Asp Ser Val Lys Gly Arg Phe Thr Ile Ser Arg Asp Asn Ala
                85                  90                  95

Lys Lys Ser Leu Tyr Leu Gln Met Asn Ser Leu Arg Ala Glu Asp Thr
            100                 105                 110
```

```
Ala Leu Tyr Tyr Cys Ala Lys Asp Ile Gln Tyr Gly Asn Tyr Tyr Tyr
            115                 120                 125

Gly Met Asp Val Trp Gly Gln Gly Thr Thr Val Thr Val Ser Ser Gly
        130                 135                 140

Gly Gly Gly Ser Gly Gly Gly Ser Gly Gly Gly Ser Gly Gly Glu Ile
145                 150                 155                 160

Val Leu Thr Gln Ser Pro Ala Thr Leu Ser Leu Ser Pro Gly Glu Arg
                165                 170                 175

Ala Thr Leu Ser Cys Arg Ala Ser Gln Ser Val Ser Ser Tyr Leu Ala
            180                 185                 190

Trp Tyr Gln Gln Lys Pro Gly Gln Ala Pro Arg Leu Leu Ile Tyr Asp
        195                 200                 205

Ala Ser Asn Arg Ala Thr Gly Ile Pro Ala Arg Phe Ser Gly Ser Gly
    210                 215                 220

Ser Gly Thr Asp Phe Thr Leu Thr Ile Ser Ser Leu Glu Pro Glu Asp
225                 230                 235                 240

Phe Ala Val Tyr Tyr Cys Gln Gln Arg Ser Asn Trp Pro Ile Thr Phe
                245                 250                 255

Gly Gln Gly Thr Arg Leu Glu Ile Lys Glu Ser Lys Tyr Gly Pro Pro
            260                 265                 270

Cys Pro Pro Cys Pro Ala Pro Glu Phe Glu Gly Gly Pro Ser Val Phe
        275                 280                 285

Leu Phe Pro Pro Lys Pro Lys Asp Thr Leu Met Ile Ser Arg Thr Pro
    290                 295                 300

Glu Val Thr Cys Val Val Val Asp Val Ser Gln Glu Asp Pro Glu Val
305                 310                 315                 320

Gln Phe Asn Trp Tyr Val Asp Gly Val Glu Val His Asn Ala Lys Thr
                325                 330                 335

Lys Pro Arg Glu Glu Gln Phe Gln Ser Thr Tyr Arg Val Val Ser Val
            340                 345                 350

Leu Thr Val Leu His Gln Asp Trp Leu Asn Gly Lys Glu Tyr Lys Cys
        355                 360                 365

Lys Val Ser Asn Lys Gly Leu Pro Ser Ser Ile Glu Lys Thr Ile Ser
    370                 375                 380

Lys Ala Lys Gly Gln Pro Arg Glu Pro Gln Val Tyr Thr Leu Pro Pro
385                 390                 395                 400

Ser Gln Glu Glu Met Thr Lys Asn Gln Val Ser Leu Thr Cys Leu Val
                405                 410                 415

Lys Gly Phe Tyr Pro Ser Asp Ile Ala Val Glu Trp Glu Ser Asn Gly
            420                 425                 430

Gln Pro Glu Asn Asn Tyr Lys Thr Thr Pro Pro Val Leu Asp Ser Asp
        435                 440                 445

Gly Ser Phe Phe Leu Tyr Ser Arg Leu Thr Val Asp Lys Ser Arg Trp
    450                 455                 460

Gln Glu Gly Asn Val Phe Ser Cys Ser Val Met His Glu Ala Leu His
465                 470                 475                 480

Asn His Tyr Thr Gln Lys Ser Leu Ser Leu Ser Leu Gly Lys Ile Tyr
                485                 490                 495

Ile Trp Ala Pro Leu Ala Gly Thr Cys Gly Val Leu Leu Leu Ser Leu
            500                 505                 510

Val Ile Thr Leu Tyr Cys Lys Arg Gly Arg Lys Lys Leu Leu Tyr Ile
        515                 520                 525

Phe Lys Gln Pro Phe Met Arg Pro Val Gln Thr Thr Gln Glu Glu Asp
```

```
                    530                  535                  540
Gly Cys Ser Cys Arg Phe Pro Glu Glu Glu Gly Gly Cys Glu Leu
545                 550                  555                 560

Arg Val Lys Phe Ser Arg Ser Ala Asp Ala Pro Ala Tyr Lys Gln Gly
                565                  570                 575

Gln Asn Gln Leu Tyr Asn Glu Leu Asn Leu Gly Arg Arg Glu Glu Tyr
            580                  585                  590

Asp Val Leu Asp Lys Arg Arg Gly Arg Asp Pro Glu Met Gly Gly Lys
                595                 600                  605

Pro Arg Arg Lys Asn Pro Gln Glu Gly Leu Tyr Asn Glu Leu Gln Lys
            610                  615                  620

Asp Lys Met Ala Glu Ala Tyr Ser Glu Ile Gly Met Lys Gly Glu Arg
625                 630                  635                 640

Arg Arg Gly Lys Gly His Asp Gly Leu Tyr Gln Gly Leu Ser Thr Ala
                645                  650                  655

Thr Lys Asp Thr Tyr Asp Ala Leu His Met Gln Ala Leu Pro Pro Arg
                660                  665                  670

<210> SEQ ID NO 6
<211> LENGTH: 2019
<212> TYPE: DNA
<213> ORGANISM: Artificial Sequence
<220> FEATURE:
<223> OTHER INFORMATION: CAR

<400> SEQUENCE: 6
atggccttac cagtgaccgc cttgctcctg ccgctggcct tgctgctcca cgccgccagg      60
ccggaagtgc agctggtgga gtctggggga ggcttggtac agcctggcag gtccctgaga     120
ctctcctgtg cagcctctgg attcaccttt aatgattatg ccatgcactg ggtccggcaa     180
gctccaggga agggcctgga gtgggtctca actattagtt ggaatagtgg ttccataggc     240
tatgcggact ctgtgaaggg ccgattcacc atctccagag acaacgccaa gaagtccctg     300
tatctgcaaa tgaacagtct gagagctgag gacacggcct tgtattactg tgcaaaagat     360
atacagtacg gcaactacta ctacggtatg gacgtctggg gccaagggac cacggtcacc     420
gtctcctcag gtggcggtgg ctcgggcggt ggtgggtcgg gtggcggcgg atctgaaatt     480
gtgttgacac agtctccagc caccctgtct ttgtctccag gggaaagagc caccctctcc     540
tgcagggcca gtcagagtgt tagcagctac ttagcctggt accaacagaa acctggccag     600
gctcccaggc tcctcatcta tgatgcatcc aacagggcca ctggcatccc agccaggttc     660
agtggcagtg ggtctgggac agacttcact ctcaccatca gcagcctaga gcctgaagat     720
tttgcagttt attactgtca gcagcgtagc aactggccga tcaccttcgg ccaagggaca     780
cgactggaga ttaaagagag caagtacgga ccgccctgcc cccttgccc tgcccccgag     840 ttcgagggcg acccagcgt gttcctgttc ccccccaagc ccaaggacac cctgatgatc     900
agccggaccc ccgaggtgac ctgcgtggtg gtggacgtga gccaggaaga tcccgaggtc     960
cagttcaatt ggtacgtgga cggcgtggaa gtgcacaacg ccaagaccaa gcccagagag    1020
gaacagttcc aaagcaccta ccgggtggtg tctgtgctga ccgtgctgca ccaggactgg    1080
ctgaacggca agaatacaa gtgcaaggtg tccaacaagg gcctgcccag cagcatcgaa    1140
aagaccatca gcaaggccaa gggccagcct cgcgagcccc aggtgtacac cctgcctccc    1200
tcccaggaag atgaccaa gaaccaggtg tccctgacct gcctggtgaa gggcttctac    1260
cccagcgaca tcgccgtgga gtgggagagc aacggccagc ctgagaacaa ctacaagacc    1320
```

```
accccteeeg tgetggacag egacggeage ttcttectgt acagccgget gacegtggac    1380 aagagccggt ggcaggaagg caacgtcttt agctgcagcg tgatgcacga ggccctgcac    1440
aaccactaca cccagaagag cctgagcctg tccctgggca agatctacat ctgggcgccc    1500
ttggccggga cttgtggggt ccttctcctg tcactggtta tcacccttta ctgcaaacgg    1560
ggcagaaaga aactcctgta tatattcaaa caaccattta tgagaccagt acaaactact    1620
caagaggaag atggctgtag ctgccgattt ccagaagaag aagaaggagg atgtgaactg    1680
agagtgaagt tcagcaggag cgcagacgcc cccgcgtaca gcagggcca gaaccagctc     1740 tataacgagc tcaatctagg acgaagagag gagtacgatg ttttggacaa gacgtggc     1800 cgggaccctg agatggggggg aaagccgaga aggaagaacc ctcaggaagg cctgtacaat    1860
gaactgcaga aagataagat ggcggaggcc tacagtgaga ttgggatgaa aggcgagcgc    1920
cggaggggca aggggcacga tggcctttac cagggtctca gtacagccac caaggacacc    1980
tacgacgccc ttcacatgca ggccctgccc cctcgctag                           2019

<210> SEQ ID NO 7
<211> LENGTH: 122
<212> TYPE: PRT
<213> ORGANISM: Artificial Sequence
<220> FEATURE:
<223> OTHER INFORMATION: Heavy chain variable region (VH)

<400> SEQUENCE: 7

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asn Asp Tyr
            20                  25                  30

Ala Met His Trp Val Arg Gln Ala Pro Gly Lys Gly Leu Glu Trp Val
        35                  40                  45

Ser Thr Ile Ser Trp Asn Ser Gly Ser Ile Gly Tyr Ala Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ile Gln Tyr Gly Asn Tyr Tyr Tyr Gly Met Asp Val Trp
            100                 105                 110

Gly Gln Gly Thr Thr Val Thr Val Ser Ser
        115                 120

<210> SEQ ID NO 8
<211> LENGTH: 366
<212> TYPE: DNA
<213> ORGANISM: Artificial Sequence
<220> FEATURE:
<223> OTHER INFORMATION: Heavy chain variable region (VH)

<400> SEQUENCE: 8
gaagtgcagc tggtggagtc tgggggaggc ttggtacagc ctggcaggtc cctgagactc     60
tcctgtgcag cctctggatt cacctttaat gattatgcca tgcactgggt ccggcaagct    120
ccagggaagg gcctggagtg gtctcaact attagttgga atagtggttc cataggctat     180
gcggactctg tgaagggccg attcaccatc tccagagaca cgccaagaa gtccctgtat      240 ctgcaaatga acagtctgag agctgaggac acggccttgt attactgtgc aaaagatata     300
```

```
cagtacggca actactacta cggtatggac gtctggggcc aagggaccac ggtcaccgtc    360
tcctca                                                               366
```

<210> SEQ ID NO 9
<211> LENGTH: 121
<212> TYPE: PRT
<213> ORGANISM: Artificial Sequence
<220> FEATURE:
<223> OTHER INFORMATION: Heavy chain variable region (VH)

<400> SEQUENCE: 9

```
Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala
        115                 120
```

<210> SEQ ID NO 10
<211> LENGTH: 363
<212> TYPE: DNA
<213> ORGANISM: Artificial Sequence
<220> FEATURE:
<223> OTHER INFORMATION: Heavy chain variable region (VH)

<400> SEQUENCE: 10

```
caggtgcagt tgcaacagcc tggagctgag ttggtgaagc ctggtgcttc tgtgaagatg     60
tcttgtaagg cttctggata cacattcact tcttacaaca tgcactgggt gaagcagact    120
cctggtaggg gtttggagtg gatcggagct atctacccag gaaacggaga cacatcttac    180
aaccagaagt tcaagggtaa ggctacattg actgctgaca agtcttcatc tactgcttac    240
atgcaattgt cttcttttgac atctgaggac tctgcagttt actactgcgc taggtctaca    300
tactacggag gtgactggta cttcaacgtg tggggagcag gtaccacggt cactgtctct    360
gca                                                                  363
```

<210> SEQ ID NO 11
<211> LENGTH: 107
<212> TYPE: PRT
<213> ORGANISM: Artificial Sequence
<220> FEATURE:
<223> OTHER INFORMATION: Light chain variable region (VL)

<400> SEQUENCE: 11

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
```

```
                35                  40                  45
Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Ile
                 85                  90                  95

Thr Phe Gly Gln Gly Thr Arg Leu Glu Ile Lys
            100                 105

<210> SEQ ID NO 12
<211> LENGTH: 321
<212> TYPE: DNA
<213> ORGANISM: Artificial Sequence
<220> FEATURE:
<223> OTHER INFORMATION: Light chain variable region (VL)

<400> SEQUENCE: 12
gaaattgtgt tgacacagtc tccagccacc ctgtctttgt ctccagggga aagagccacc      60
ctctcctgca gggccagtca gagtgttagc agctacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ctgtcagcag cgtagcaact ggccgatcac cttcggccaa     300
gggacacgac tggagattaa a                                               321

<210> SEQ ID NO 13
<211> LENGTH: 106
<212> TYPE: PRT
<213> ORGANISM: Artificial Sequence
<220> FEATURE:
<223> OTHER INFORMATION: Light chain variable region (VL)

<400> SEQUENCE: 13

Gln Ile Val Leu Ser Gln Ser Pro Ala Ile Leu Ser Ala Ser Pro Gly
 1               5                  10                  15

Glu Lys Val Thr Met Thr Cys Arg Ala Ser Ser Ser Val Ser Tyr Ile
                20                  25                  30

His Trp Phe Gln Gln Lys Pro Gly Ser Ser Pro Lys Pro Trp Ile Tyr
            35                  40                  45

Ala Thr Ser Asn Leu Ala Ser Gly Val Pro Val Arg Phe Ser Gly Ser
 50                  55                  60

Gly Ser Gly Thr Ser Tyr Ser Leu Thr Ile Ser Arg Val Glu Ala Glu
 65                  70                  75                  80

Asp Ala Ala Thr Tyr Tyr Cys Gln Gln Trp Thr Ser Asn Pro Pro Thr
                 85                  90                  95

Phe Gly Gly Gly Thr Lys Leu Glu Ile Lys
            100                 105

<210> SEQ ID NO 14
<211> LENGTH: 318
<212> TYPE: DNA
<213> ORGANISM: Artificial Sequence
<220> FEATURE:
<223> OTHER INFORMATION: Light chain variable region (VL)

<400> SEQUENCE: 14
caaattgttc tctcccagtc tccagcaatc ctgtcagctt ctcctggaga aaggtgact      60
```

```
atgacttgca  gggcttcttc  atctgtttct  tacatccact  ggttccagca  gaagcctggt    120
tcttcaccta  agcctggat   ctacgctaca  tctaacttgg  catctggagt  gcctgtgagg    180
ttctctggtt  ctggttcagg  tacttcttac  tctttgacaa  tctctagggt  ggaggctgag    240
gacgctgcta  cttactactg  ccagcagtgg  acatctaacc  ctccaacatt  cggaggtggt    300
actaagttgg  agatcaag                                                      318
```

<210> SEQ ID NO 15
<211> LENGTH: 15
<212> TYPE: PRT
<213> ORGANISM: Artificial Sequence
<220> FEATURE:
<223> OTHER INFORMATION: Linker Peptide

<400> SEQUENCE: 15

```
Gly Gly Gly Gly Ser Gly Gly Gly Gly Ser Gly Gly Gly Gly Ser
1               5                   10                  15
```

<210> SEQ ID NO 16
<211> LENGTH: 45
<212> TYPE: DNA
<213> ORGANISM: Artificial Sequence
<220> FEATURE:
<223> OTHER INFORMATION: Linker Peptide

<400> SEQUENCE: 16

```
ggtggcggtg  gctcgggcgg  tggtgggtcg  ggtggcggcg  gatct                      45
```

<210> SEQ ID NO 17
<211> LENGTH: 229
<212> TYPE: PRT
<213> ORGANISM: Artificial Sequence
<220> FEATURE:
<223> OTHER INFORMATION: Hinge region (H)

<400> SEQUENCE: 17

```
Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
```

```
            180                 185                 190
Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225
```

```
<210> SEQ ID NO 18
<211> LENGTH: 687
<212> TYPE: DNA
<213> ORGANISM: Artificial Sequence
<220> FEATURE:
<223> OTHER INFORMATION: Hinge region (H)

<400> SEQUENCE: 18
gagagcaagt acggaccgcc ctgcccccct tgccctgccc ccgagttcct gggcggaccc      60
agcgtgttcc tgttcccccc caagcccaag acaccctga tgatcagccg gaccccgag      120 gtgacctgcg tggtggtgga cgtgagccag gaagatcccg aggtccagtt caattggtac    180
gtggacggcg tggaagtgca caacgccaag accaagccca gagaggaaca gttcaacagc    240
acctaccggg tggtgtctgt gctgaccgtg ctgcaccagg actggctgaa cggcaaagaa    300
tacaagtgca aggtgtccaa caagggcctg cccagcagca tcgaaaagac catcagcaag    360
gccaagggcc agcctcgcga gccccaggtg tacaccctgc ctccctccca ggaagagatg    420
accaagaacc aggtgtccct gacctgcctg gtgaagggct tctacccag cgacatcgcc     480 gtggagtggg agagcaacgg ccagcctgag aacaactaca agaccacccc tcccgtgctg    540
gacagcgacg gcagcttctt cctgtacagc cggctgaccg tggacaagag ccggtggcag    600
gaaggcaacg tctttagctg cagcgtgatg cacgaggccc tgcacaacca ctacacccag    660
aagagcctga gcctgtccct gggcaag                                        687
```

```
<210> SEQ ID NO 19
<211> LENGTH: 229
<212> TYPE: PRT
<213> ORGANISM: Artificial Sequence
<220> FEATURE:
<223> OTHER INFORMATION: Hinge region (H)

<400> SEQUENCE: 19

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Gln Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125
```

```
Gln Val Tyr Thr Leu Pro Pro Ser Gln Glu Glu Met Thr Lys Asn Gln
            130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
                195                 200                 205

Val Met His Glu Ala Leu His Asn His Tyr Thr Gln Lys Ser Leu Ser
            210                 215                 220

Leu Ser Leu Gly Lys
225

<210> SEQ ID NO 20
<211> LENGTH: 687
<212> TYPE: DNA
<213> ORGANISM: Artificial Sequence
<220> FEATURE:
<223> OTHER INFORMATION: Hinge region (H)

<400> SEQUENCE: 20
gagagcaagt acggaccgcc ctgccccct  tgccctgccc ccgagttcga gggcggaccc      60
agcgtgttcc tgttcccccc caagcccaag acaccctga  tgatcagccg gaccccgag     120 gtgacctgcg tggtggtgga cgtgagccag gaagatcccg aggtccagtt caattggtac     180
gtggacggcg tggaagtgca caacgccaag accaagccca gagaggaaca gttccaaagc     240
acctaccggg tggtgtctgt gctgaccgtg ctgcaccagg actggctgaa cggcaaagaa     300
tacaagtgca aggtgtccaa caagggcctg cccagcagca tcgaaaagac catcagcaag     360
gccaagggcc agcctcgcga gccccaggtg tacaccctgc ctccctccca ggaagagatg     420
accaagaacc aggtgtccct gacctgcctg gtgaagggct cctaccccag cgacatcgcc     480
gtggagtggg agagcaacgg ccagcctgag aacaactaca agaccacccc tcccgtgctg     540
gacagcgacg gcagcttctt cctgtacagc cggctgaccg tggacaagag ccggtggcag     600
gaaggcaacg tctttagctg cagcgtgatg cacgaggccc tgcacaacca ctacacccag     660
aagagcctga gcctgtccct gggcaag                                         687

<210> SEQ ID NO 21
<211> LENGTH: 24
<212> TYPE: PRT
<213> ORGANISM: Artificial Sequence
<220> FEATURE:
<223> OTHER INFORMATION: Transmembrane domain (TM)

<400> SEQUENCE: 21

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 22
<211> LENGTH: 72
<212> TYPE: DNA
<213> ORGANISM: Artificial Sequence
<220> FEATURE:
<223> OTHER INFORMATION: Transmembrane domain (TM)
```

<400> SEQUENCE: 22
atctacatct gggcgcccct tggccgggact tgtggggtcc ttctcctgtc actggttatc    60 acccttttact gc    72

<210> SEQ ID NO 23
<211> LENGTH: 42
<212> TYPE: PRT
<213> ORGANISM: Artificial Sequence
<220> FEATURE:
<223> OTHER INFORMATION: Co-stimulatory molecule (CS)

<400> SEQUENCE: 23

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 24
<211> LENGTH: 126
<212> TYPE: DNA
<213> ORGANISM: Artificial Sequence
<220> FEATURE:
<223> OTHER INFORMATION: Co-stimulatory molecule (CS)

<400> SEQUENCE: 24
aaacggggca gaaagaaact cctgtatata ttcaaacaac catttatgag accagtacaa    60
actactcaag aggaagatgg ctgtagctgc cgatttccag aagaagaaga aggaggatgt   120
gaactg    126

<210> SEQ ID NO 25
<211> LENGTH: 113
<212> TYPE: PRT
<213> ORGANISM: Artificial Sequence
<220> FEATURE:
<223> OTHER INFORMATION: CD3zeta

<400> SEQUENCE: 25

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Gln Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg

<210> SEQ ID NO 26
<211> LENGTH: 336
<212> TYPE: DNA
<213> ORGANISM: Artificial Sequence
<220> FEATURE:
<223> OTHER INFORMATION: CD3zeta

<400> SEQUENCE: 26

```
agagtgaagt tcagcaggag cgcagacgcc cccgcgtaca agcagggcca gaaccagctc    60
tataacgagc tcaatctagg acgaagagag gagtacgatg ttttggacaa gagacgtggc   120
cgggaccctg agatggggggg aaagccgaga aggaagaacc ctcaggaagg cctgtacaat   180
gaactgcaga aagataagat ggcggaggcc tacagtgaga ttgggatgaa aggcgagcgc   240
cggagggggca aggggcacga tggcctttac cagggtctca gtacagccac caaggacacc   300
tacgacgccc ttcacatgca ggccctgccc cctcgc                              336
```

<210> SEQ ID NO 27
<211> LENGTH: 21
<212> TYPE: PRT
<213> ORGANISM: Artificial Sequence
<220> FEATURE:
<223> OTHER INFORMATION: Leader (L)

<400> SEQUENCE: 27

Met Ala Leu Pro Val Thr Ala Leu Leu Leu Pro Leu Ala Leu Leu Leu
1               5                   10                  15
His Ala Ala Arg Pro
            20

<210> SEQ ID NO 28
<211> LENGTH: 63
<212> TYPE: DNA
<213> ORGANISM: Artificial Sequence
<220> FEATURE:
<223> OTHER INFORMATION: Leader (L)

<400> SEQUENCE: 28

```
atggccttac cagtgaccgc cttgctcctg ccgctggcct tgctgctcca cgccgccagg    60
ccg                                                                  63
```

<210> SEQ ID NO 29
<211> LENGTH: 677
<212> TYPE: PRT
<213> ORGANISM: Artificial Sequence
<220> FEATURE:
<223> OTHER INFORMATION: CAR

<400> SEQUENCE: 29

Met Ala Leu Pro Val Thr Ala Leu Leu Leu Pro Leu Ala Leu Leu Leu
1               5                   10                  15
His Ala Ala Arg Pro Gln Val Gln Leu Val Gln Ser Gly Ala Glu Val
            20                  25                  30
Lys Lys Pro Gly Ser Ser Val Lys Val Ser Cys Lys Ala Ser Gly Tyr
        35                  40                  45
Ala Phe Ser Tyr Ser Trp Ile Asn Trp Val Arg Gln Ala Pro Gly Gln
    50                  55                  60
Gly Leu Glu Trp Met Gly Arg Ile Phe Pro Gly Asp Gly Asp Thr Asp
65                  70                  75                  80
Tyr Asn Gly Lys Phe Lys Gly Arg Val Thr Ile Thr Ala Asp Lys Ser
                85                  90                  95
Thr Ser Thr Ala Tyr Met Glu Leu Ser Ser Leu Arg Ser Glu Asp Thr
            100                 105                 110
Ala Val Tyr Tyr Cys Ala Arg Asn Val Phe Asp Gly Tyr Trp Leu Val

-continued

```
            115                 120                 125
Tyr Trp Gly Gln Gly Thr Leu Val Thr Val Ser Ser Gly Gly Gly
    130                 135                 140
Ser Gly Gly Gly Gly Ser Gly Gly Gly Gly Ser Asp Ile Val Met Thr
145                 150                 155                 160
Gln Thr Pro Leu Ser Leu Pro Val Thr Pro Gly Glu Pro Ala Ser Ile
                165                 170                 175
Ser Cys Arg Ser Ser Lys Ser Leu Leu His Ser Asn Gly Ile Thr Tyr
                180                 185                 190
Leu Tyr Trp Tyr Leu Gln Lys Pro Gly Gln Ser Pro Gln Leu Leu Ile
                195                 200                 205
Tyr Gln Met Ser Asn Leu Val Ser Gly Val Pro Asp Arg Phe Ser Gly
            210                 215                 220
Ser Gly Ser Gly Thr Asp Phe Thr Leu Lys Ile Ser Arg Val Glu Ala
225                 230                 235                 240
Glu Asp Val Gly Val Tyr Tyr Cys Ala Gln Asn Leu Glu Leu Pro Tyr
                245                 250                 255
Thr Phe Gly Gly Gly Thr Lys Val Glu Ile Lys Arg Thr Val Glu Ser
                260                 265                 270
Lys Tyr Gly Pro Pro Cys Pro Pro Cys Pro Ala Pro Glu Phe Leu Gly
                275                 280                 285
Gly Pro Ser Val Phe Leu Phe Pro Pro Lys Pro Lys Asp Thr Leu Met
290                 295                 300
Ile Ser Arg Thr Pro Glu Val Thr Cys Val Val Val Asp Val Ser Gln
305                 310                 315                 320
Glu Asp Pro Glu Val Gln Phe Asn Trp Tyr Val Asp Gly Val Glu Val
                325                 330                 335
His Asn Ala Lys Thr Lys Pro Arg Glu Glu Gln Phe Asn Ser Thr Tyr
            340                 345                 350
Arg Val Val Ser Val Leu Thr Val Leu His Gln Asp Trp Leu Asn Gly
            355                 360                 365
Lys Glu Tyr Lys Cys Lys Val Ser Asn Lys Gly Leu Pro Ser Ser Ile
    370                 375                 380
Glu Lys Thr Ile Ser Lys Ala Lys Gly Gln Pro Arg Glu Pro Gln Val
385                 390                 395                 400
Tyr Thr Leu Pro Pro Ser Gln Glu Glu Met Thr Lys Asn Gln Val Ser
                405                 410                 415
Leu Thr Cys Leu Val Lys Gly Phe Tyr Pro Ser Asp Ile Ala Val Glu
                420                 425                 430
Trp Glu Ser Asn Gly Gln Pro Glu Asn Asn Tyr Lys Thr Thr Pro Pro
            435                 440                 445
Val Leu Asp Ser Asp Gly Ser Phe Phe Leu Tyr Ser Arg Leu Thr Val
    450                 455                 460
Asp Lys Ser Arg Trp Gln Glu Gly Asn Val Phe Ser Cys Ser Val Met
465                 470                 475                 480
His Glu Ala Leu His Asn His Tyr Thr Gln Lys Ser Leu Ser Leu Ser
                485                 490                 495
Leu Gly Lys Ile Tyr Ile Trp Ala Pro Leu Ala Gly Thr Cys Gly Val
                500                 505                 510
Leu Leu Leu Ser Leu Val Ile Thr Leu Tyr Cys Lys Arg Gly Arg Lys
            515                 520                 525
Lys Leu Leu Tyr Ile Phe Lys Gln Pro Phe Met Arg Pro Val Gln Thr
            530                 535                 540
```

Thr Gln Glu Glu Asp Gly Cys Ser Cys Arg Phe Pro Glu Glu Glu
545                 550                 555                 560

Gly Gly Cys Glu Leu Arg Val Lys Phe Ser Arg Ser Ala Asp Ala Pro
            565                 570                 575

Ala Tyr Lys Gln Gly Gln Asn Gln Leu Tyr Asn Glu Leu Asn Leu Gly
        580                 585                 590

Arg Arg Glu Glu Tyr Asp Val Leu Asp Lys Arg Arg Gly Arg Asp Pro
    595                 600                 605

Glu Met Gly Gly Lys Pro Arg Arg Lys Asn Pro Gln Glu Gly Leu Tyr
610                 615                 620

Asn Glu Leu Gln Lys Asp Lys Met Ala Glu Ala Tyr Ser Glu Ile Gly
625                 630                 635                 640

Met Lys Gly Glu Arg Arg Arg Gly Lys Gly His Asp Gly Leu Tyr Gln
            645                 650                 655

Gly Leu Ser Thr Ala Thr Lys Asp Thr Tyr Asp Ala Leu His Met Gln
        660                 665                 670

Ala Leu Pro Pro Arg
        675

<210> SEQ ID NO 30
<211> LENGTH: 2034
<212> TYPE: DNA
<213> ORGANISM: Artificial Sequence
<220> FEATURE:
<223> OTHER INFORMATION: CAR

<400> SEQUENCE: 30 atggcctfac cagtgaccgc cttgctcctg ccgctggcct tgctgctcca cgccgccagg     60
ccgcaggtgc aattggtgca gtctggcgct gaagttaaga gcctgggag ttcagtgaag    120 gtctcctgca aggcttccgg atacgccttc agctattctt ggatcaattg ggtgcggcag    180
gcgcctggac aagggctcga gtggatggga cggatctttc ccggcgatgg ggatactgac    240
tacaatggga aattcaaggg cagagtcaca attaccgccg acaaatccac tagcacagcc    300
tatatggagc tgagcagcct gagatctgag gacacggccg tgtattactg tgcaagaaat    360
gtctttgatg gttactggct tgtttactgg ggccagggaa ccctggtcac cgtctcctca    420
ggtggcggtg gctcgggcgg tgtgggtcg gtggcggcg gatctgatat cgtgatgacc    480
cagactccac tctccctgcc cgtcacccct ggagagcccg ccagcattag ctgcaggtct    540
agcaagagcc tcttgcacag caatggcatc acttatttgt attggtacct gcaaaagcca    600
gggcagtctc cacagctcct gatttatcaa atgtccaacc ttgtctctgg cgtccctgac    660
cggttctccg gctccgggtc aggcactgat ttcacactga aaatcagcag ggtggaggct    720
gaggatgttg gagtttatta ctgcgctcag aatctagaac ttccttacac cttcggcgga    780
gggaccaagg tggagatcaa acgtacggtg gagagcaagt acggaccgcc ctgccccct    840 tgccctgccc ccgagttcct gggcggaccc agcgtgttcc tgttccccc caagcccaag    900 gacacctga tgatcagccg gacccccgag gtgacctgcg tggtggtgga cgtgagccag    960
gaagatcccg aggtccagtt caattggtac gtggacggcg tggaagtgca caacgccaag   1020
accaagccca gagaggaaca gttcaacagc acctaccggg tggtgtctgt gctgaccgtg   1080
ctgcaccagg actggctgaa cggcaaagaa tacaagtgca aggtgtccaa caagggcctg   1140
cccagcagca tcgaaaagac catcagcaag gccaagggcc agcctcgcga gccccaggtg   1200
tacaccctgc ctcccttcca ggaagagatg accaagaacc aggtgtccct gacctgcctg   1260

```
gtgaagggct tctacccag cgacatcgcc gtggagtggg agagcaacgg ccagcctgag    1320
aacaactaca agaccacccc tcccgtgctg gacagcgacg gcagcttctt cctgtacagc    1380
cggctgaccg tggacaagag ccggtggcag gaaggcaacg tctttagctg cagcgtgatg    1440
cacgaggccc tgcacaacca ctacacccag aagagcctga gcctgtccct gggcaagatc    1500
tacatctggg cgcccttggc cgggacttgt ggggtccttc tcctgtcact ggttatcacc    1560
ctttactgca acggggcag aaagaaactc ctgtatatat tcaaacaacc atttatgaga    1620
ccagtacaaa ctactcaaga ggaagatggc tgtagctgcc gatttccaga agaagaagaa    1680
ggaggatgtg aactgagagt gaagttcagc aggagcgcag acgccccgc gtacaagcag    1740 ggccagaacc agctctataa cgagctcaat ctaggacgaa gagaggagta cgatgttttg    1800
gacaagagac gtggccggga ccctgagatg gggggaaagc cgagaaggaa gaaccctcag    1860
gaaggcctgt acaatgaact gcagaaagat aagatggcgg aggcctacag tgagattggg    1920
atgaaaggcg agcgccggag gggcaagggg cacgatggcc tttaccaggg tctcagtaca    1980
gccaccaagg acacctacga cgcccttcac atgcaggccc tgccccctcg ctag          2034
```

<210> SEQ ID NO 31
<211> LENGTH: 716
<212> TYPE: PRT
<213> ORGANISM: Artificial Sequence
<220> FEATURE:
<223> OTHER INFORMATION: CAR

<400> SEQUENCE: 31

```
Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Pro Gly Arg Ser Leu Arg Leu Ser Cys Ala Ala Ser Gly Phe
        35                  40                  45

Thr Phe Asn Asp Tyr Ala Met His Trp Val Arg Gln Ala Pro Gly Lys
    50                  55                  60

Gly Leu Glu Trp Val Ser Thr Ile Ser Trp Asn Ser Gly Ser Ile Gly
65                  70                  75                  80

Tyr Ala Asp Ser Val Lys Gly Arg Phe Thr Ile Ser Arg Asp Asn Ala
                85                  90                  95

Lys Lys Ser Leu Tyr Leu Gln Met Asn Ser Leu Arg Ala Glu Asp Thr
            100                 105                 110

Ala Leu Tyr Tyr Cys Ala Lys Asp Ile Gln Tyr Gly Asn Tyr Tyr Tyr
        115                 120                 125

Gly Met Asp Val Trp Gly Gln Gly Thr Thr Val Thr Val Ser Ser Gly
    130                 135                 140

Gly Gly Gly Ser Gly Gly Gly Ser Gly Gly Gly Ser Glu Ile
145                 150                 155                 160

Val Leu Thr Gln Ser Pro Ala Thr Leu Ser Leu Ser Pro Gly Glu Arg
                165                 170                 175

Ala Thr Leu Ser Cys Arg Ala Ser Gln Ser Val Ser Ser Tyr Leu Ala
            180                 185                 190

Trp Tyr Gln Gln Lys Pro Gly Gln Ala Pro Arg Leu Leu Ile Tyr Asp
        195                 200                 205

Ala Ser Asn Arg Ala Thr Gly Ile Pro Ala Arg Phe Ser Gly Ser Gly
    210                 215                 220
```

```
Ser Gly Thr Asp Phe Thr Leu Thr Ile Ser Ser Leu Glu Pro Glu Asp
225                 230                 235                 240

Phe Ala Val Tyr Tyr Cys Gln Gln Arg Ser Asn Trp Pro Ile Thr Phe
            245                 250                 255

Gly Gln Gly Thr Arg Leu Glu Ile Lys Glu Ser Lys Tyr Gly Pro Pro
        260                 265                 270

Cys Pro Pro Cys Pro Ala Pro Glu Phe Glu Gly Gly Pro Ser Val Phe
    275                 280                 285

Leu Phe Pro Pro Lys Pro Lys Asp Thr Leu Met Ile Ser Arg Thr Pro
290                 295                 300

Glu Val Thr Cys Val Val Val Asp Val Ser Gln Glu Asp Pro Glu Val
305                 310                 315                 320

Gln Phe Asn Trp Tyr Val Asp Gly Val Glu Val His Asn Ala Lys Thr
            325                 330                 335

Lys Pro Arg Glu Glu Gln Phe Gln Ser Thr Tyr Arg Val Val Ser Val
        340                 345                 350

Leu Thr Val Leu His Gln Asp Trp Leu Asn Gly Lys Glu Tyr Lys Cys
    355                 360                 365

Lys Val Ser Asn Lys Gly Leu Pro Ser Ser Ile Glu Lys Thr Ile Ser
370                 375                 380

Lys Ala Lys Gly Gln Pro Arg Glu Pro Gln Val Tyr Thr Leu Pro Pro
385                 390                 395                 400

Ser Gln Glu Glu Met Thr Lys Asn Gln Val Ser Leu Thr Cys Leu Val
            405                 410                 415

Lys Gly Phe Tyr Pro Ser Asp Ile Ala Val Glu Trp Glu Ser Asn Gly
        420                 425                 430

Gln Pro Glu Asn Asn Tyr Lys Thr Thr Pro Pro Val Leu Asp Ser Asp
    435                 440                 445

Gly Ser Phe Phe Leu Tyr Ser Arg Leu Thr Val Asp Lys Ser Arg Trp
450                 455                 460

Gln Glu Gly Asn Val Phe Ser Cys Ser Val Met His Glu Ala Leu His
465                 470                 475                 480

Asn His Tyr Thr Gln Lys Ser Leu Ser Leu Ser Leu Gly Lys Phe Trp
            485                 490                 495

Val Leu Val Val Val Gly Gly Val Leu Ala Cys Tyr Ser Leu Leu Val
        500                 505                 510

Thr Val Ala Phe Ile Ile Phe Trp Val Arg Ser Lys Arg Ser Arg Leu
    515                 520                 525

Leu His Ser Asp Tyr Met Asn Met Thr Pro Arg Arg Pro Gly Pro Thr
530                 535                 540

Arg Lys His Tyr Gln Pro Tyr Ala Pro Pro Arg Asp Phe Ala Ala Tyr
545                 550                 555                 560

Arg Ser Lys Arg Gly Arg Lys Lys Leu Leu Tyr Ile Phe Lys Gln Pro
            565                 570                 575

Phe Met Arg Pro Val Gln Thr Thr Gln Glu Glu Asp Gly Cys Ser Cys
        580                 585                 590

Arg Phe Pro Glu Glu Glu Glu Gly Gly Cys Glu Leu Arg Val Lys Phe
    595                 600                 605

Ser Arg Ser Ala Asp Ala Pro Ala Tyr Lys Gln Gly Gln Asn Gln Leu
610                 615                 620

Tyr Asn Glu Leu Asn Leu Gly Arg Arg Glu Glu Tyr Asp Val Leu Asp
625                 630                 635                 640

Lys Arg Arg Gly Arg Asp Pro Glu Met Gly Gly Lys Pro Arg Arg Lys
```

|     | 645 |     |     |     | 650 |     |     |     | 655 |     |     |
|-----|-----|-----|-----|-----|-----|-----|-----|-----|-----|-----|-----|

Asn Pro Gln Glu Gly Leu Tyr Asn Glu Leu Gln Lys Asp Lys Met Ala
              660                 665                 670

Glu Ala Tyr Ser Glu Ile Gly Met Lys Gly Glu Arg Arg Arg Gly Lys
            675                 680                 685

Gly His Asp Gly Leu Tyr Gln Gly Leu Ser Thr Ala Thr Lys Asp Thr
        690                 695                 700

Tyr Asp Ala Leu His Met Gln Ala Leu Pro Pro Arg
705                 710                 715

<210> SEQ ID NO 32
<211> LENGTH: 2151
<212> TYPE: DNA
<213> ORGANISM: Artificial Sequence
<220> FEATURE:
<223> OTHER INFORMATION: CAR

<400> SEQUENCE: 32

| | | | | | |
|---|---|---|---|---|---|
| atggccttac | cagtgaccgc | cttgctcctg | ccgctggcct | tgctgctcca | cgccgccagg | 60 |
| ccggaagtgc | agctggtgga | gtctggggga | ggcttggtac | agcctggcag | gtccctgaga | 120 |
| ctctcctgtg | cagcctctgg | attcaccttt | aatgattatg | ccatgcactg | ggtccggcaa | 180 |
| gctccaggga | agggcctgga | gtgggtctca | actattagtt | ggaatagtgg | ttccataggc | 240 |
| tatgcggact | ctgtgaaggg | ccgattcacc | atctccagag | acaacgccaa | gaagtccctg | 300 |
| tatctgcaaa | tgaacagtct | gagagctgag | gacacggcct | tgtattactg | tgcaaaagat | 360 |
| atacagtacg | gcaactacta | ctacggtatg | gacgtctggg | gccaagggac | cacggtcacc | 420 |
| gtctcctcag | gtggcggtgg | ctcgggcggt | ggtgggtcgg | gtggcggcgg | atctgaaatt | 480 |
| gtgttgacac | agtctccagc | caccctgtct | ttgtctccag | ggaaagagc | caccctctcc | 540 |
| tgcagggcca | gtcagagtgt | tagcagctac | ttagcctggt | accaacagaa | acctggccag | 600 |
| gctcccaggc | tcctcatcta | tgatgcatcc | aacagggcca | ctggcatccc | agccaggttc | 660 |
| agtggcagtg | ggtctgggac | agacttcact | ctcaccatca | gcagcctaga | gcctgaagat | 720 |
| tttgcagttt | attactgtca | gcagcgtagc | aactggccga | tcaccttcgg | ccaagggaca | 780 |
| cgactggaga | ttaaagagag | caagtacgga | ccgccctgcc | cccttgccc | tgcccccgag | 840 |
| ttcgagggcg | acccagcgt | gttcctgttc | cccccaagc | caaggacac | cctgatgatc | 900 |
| agccggaccc | ccgaggtgac | ctgcgtggtg | gtggacgtga | gccaggaaga | tcccgaggtc | 960 |
| cagttcaatt | ggtacgtgga | cggcgtgaa | gtgcacaacg | ccaagaccaa | gccagagag | 1020 |
| gaacagttcc | aaagcaccta | ccgggtggtg | tctgtgctga | ccgtgctgca | ccaggactgg | 1080 |
| ctgaacggca | agaatacaa | gtgcaaggtg | tccaacaagg | gcctgcccag | cagcatcgaa | 1140 |
| aagaccatca | gcaaggccaa | gggccagcct | cgcgagcccc | aggtgtacac | cctgcctccc | 1200 |
| tcccaggaag | agatgaccaa | gaaccaggtg | tccctgacct | gcctggtgaa | gggcttctac | 1260 |
| cccagcgaca | tcgccgtgga | gtgggagagc | aacggccagc | ctgagaacaa | ctacaagacc | 1320 |
| acccctcccg | tgctggacag | cgacggcagc | ttcttcctgt | acagccggct | gaccgtggac | 1380 |
| aagagccggt | ggcaggaagg | caacgtcttt | agctgcagcg | tgatgcacga | ggccctgcac | 1440 |
| aaccactaca | cccagaagag | cctgagcctg | tccctgggca | gttttgggt | gctggtggtg | 1500 |
| gttggtggag | tcctggcttg | ctatagcttg | ctagtaacag | tggcctttat | tattttctgg | 1560 |
| gtgaggagta | gaggagcag | gctcctgcac | agtgactaca | tgaacatgac | tccccgccgc | 1620 |
| cccgggccca | cccgcaagca | ttaccagccc | tatgcccac | cacgcgactt | cgcagcctat | 1680 |

```
cgctccaaac ggggcagaaa gaaactcctg tatatattca acaaccatt tatgagacca    1740 gtacaaacta ctcaagagga agatggctgt agctgccgat tccagaaga agaagaagga    1800 ggatgtgaac tgagagtgaa gttcagcagg agcgcagacg ccccgcgta caagcagggc    1860 cagaaccagc tctataacga gctcaatcta ggacgaagag aggagtacga tgttttggac    1920
aagagacgtg gccgggaccc tgagatgggg ggaaagccga aaggaagaa ccctcaggaa     1980 ggcctgtaca atgaactgca gaaagataag atggcggagg cctacagtga gattgggatg    2040
aaaggcgagc gccggagggg caaggggcac gatggccttt accagggtct cagtacagcc    2100
accaaggaca cctacgacgc ccttcacatg caggccctgc ccctcgcta a              2151
```

<210> SEQ ID NO 33
<211> LENGTH: 119
<212> TYPE: PRT
<213> ORGANISM: Artificial Sequence
<220> FEATURE:
<223> OTHER INFORMATION: Heavy chain variable region (VH)

<400> SEQUENCE: 33

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115
```

<210> SEQ ID NO 34
<211> LENGTH: 357
<212> TYPE: DNA
<213> ORGANISM: Artificial Sequence
<220> FEATURE:
<223> OTHER INFORMATION: Heavy chain variable region (VH)

<400> SEQUENCE: 34

```
caggtgcaat tggtgcagtc tggcgctgaa gttaagaagc ctgggagttc agtgaaggtc    60
tcctgcaagg cttccggata cgccttcagc tattcttgga tcaattgggt gcggcaggcg    120
cctggacaag gctcgagtg gatgggacgg atctttcccg gcgatgggga tactgactac    180
aatgggaaat tcaagggcag agtcacaatt accgccgaca atccactag cacagcctat    240 atggagctga gcagcctgag atctgaggac acggccgtgt attactgtgc aagaaatgtc    300
tttgatggtt actggcttgt ttactggggc cagggaaccc tggtcaccgt ctcctca       357
```

<210> SEQ ID NO 35
<211> LENGTH: 115
<212> TYPE: PRT
<213> ORGANISM: Artificial Sequence
<220> FEATURE:

<223> OTHER INFORMATION: Light chain variable region (VL)

<400> SEQUENCE: 35

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
            100                 105                 110

Arg Thr Val
        115

<210> SEQ ID NO 36
<211> LENGTH: 345
<212> TYPE: DNA
<213> ORGANISM: Artificial Sequence
<220> FEATURE:
<223> OTHER INFORMATION: Light chain variable region (VL)

<400> SEQUENCE: 36
gatatcgtga tgacccagac tccactctcc ctgcccgtca cccctggaga gcccgccagc      60
attagctgca ggtctagcaa gagcctcttg cacagcaatg gcatcactta tttgtattgg    120
tacctgcaaa agccagggca gtctccacag ctcctgattt atcaaatgtc caaccttgtc    180
tctggcgtcc ctgaccggtt ctccggctcc gggtcaggca ctgatttcac actgaaaatc    240
agcagggtgg aggctgagga tgttggagtt tattactgcg ctcagaatct agaacttcct    300
tacaccttcg gcggagggac caaggtggag atcaaacgta cggtg                    345

<210> SEQ ID NO 37
<211> LENGTH: 27
<212> TYPE: PRT
<213> ORGANISM: Artificial Sequence
<220> FEATURE:
<223> OTHER INFORMATION: Transmembrane domain (TM)

<400> SEQUENCE: 37

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 38
<211> LENGTH: 81
<212> TYPE: DNA
<213> ORGANISM: Artificial Sequence
<220> FEATURE:
<223> OTHER INFORMATION: Transmembrane domain (TM)

<400> SEQUENCE: 38
ttttgggtgc tggtggtggt tggtggagtc ctggcttgct atagcttgct agtaacagtg      60
gcctttatta ttttctgggt g                                                81

```
<210> SEQ ID NO 39
<211> LENGTH: 41
<212> TYPE: PRT
<213> ORGANISM: Artificial Sequence
<220> FEATURE:
<223> OTHER INFORMATION: Co-stimulatory molecule (CS)

<400> SEQUENCE: 39

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 40
<211> LENGTH: 123
<212> TYPE: DNA
<213> ORGANISM: Artificial Sequence
<220> FEATURE:
<223> OTHER INFORMATION: Co-stimulatory molecule (CS)

<400> SEQUENCE: 40
aggagtaaga ggagcaggct cctgcacagt gactacatga acatgactcc ccgccgcccc         60
gggcccaccc gcaagcatta ccagccctat gccccaccac gcgacttcgc agcctatcgc        120
tcc                                                                     123
```